US011437581B2

(12) United States Patent
Bai

(10) Patent No.: US 11,437,581 B2
(45) Date of Patent: Sep. 6, 2022

(54) BLUE FLUORESCENT MATERIAL AND DISPLAY PANEL

(71) Applicant: WUHAN CHINA STAR OPTOELECTRONICS SEMICONDUCTOR DISPLAY TECHNOLOGY CO., LTD., Hubei (CN)

(72) Inventor: Keyan Bai, Hubei (CN)

(73) Assignee: WUHAN CHINA STAR OPTOELECTRONICS SEMICONDUCTOR DISPLAY TECHNOLOGY CO., LTD., Hubei (CN)

(*) Notice: Subject to any disclaimer, the term of this patent is extended or adjusted under 35 U.S.C. 154(b) by 211 days.

(21) Appl. No.: 16/611,520

(22) PCT Filed: Sep. 25, 2019

(86) PCT No.: PCT/CN2019/107771
§ 371 (c)(1),
(2) Date: Nov. 7, 2019

(87) PCT Pub. No.: WO2020/237936
PCT Pub. Date: Dec. 3, 2020

(65) Prior Publication Data
US 2020/0373495 A1 Nov. 26, 2020

(30) Foreign Application Priority Data
May 24, 2019 (CN) .......................... 201910437252.3

(51) Int. Cl.
| | |
|---|---|
| *H01L 51/00* | (2006.01) |
| *C07C 211/45* | (2006.01) |
| *C07C 209/68* | (2006.01) |
| *C09K 11/06* | (2006.01) |
| *C07D 209/86* | (2006.01) |
| *C07D 209/88* | (2006.01) |
| *C07D 219/02* | (2006.01) |
| *C07D 235/18* | (2006.01) |
| *C07D 249/08* | (2006.01) |
| *H01L 27/32* | (2006.01) |
| *H01L 51/50* | (2006.01) |

(52) U.S. Cl.
CPC ........ *H01L 51/0054* (2013.01); *C07C 209/68* (2013.01); *C07C 211/45* (2013.01); *C07D 209/86* (2013.01); *C07D 209/88* (2013.01); *C07D 219/02* (2013.01); *C07D 235/18* (2013.01); *C07D 249/08* (2013.01); *C09K 11/06* (2013.01); *H01L 27/3211* (2013.01); *H01L 51/006* (2013.01); *H01L 51/0067* (2013.01); *H01L 51/0072* (2013.01); *C07C 2601/14* (2017.05); *C07C 2603/50* (2017.05); *C09K 2211/1007* (2013.01); *C09K 2211/1011* (2013.01); *C09K 2211/1014* (2013.01); *C09K 2211/1018* (2013.01); *H01L 51/5012* (2013.01)

(58) Field of Classification Search
CPC ............ H01L 51/0054; H01L 27/3211; H01L 51/006; H01L 51/0067; H01L 51/0072; H01L 51/5012; C07C 209/68; C07C 2603/50; C07C 2601/14; C07C 211/45; C07D 209/86; C07D 209/88; C07D 219/02; C07D 235/18; C07D 249/08; C09K 11/06; C09K 2211/1007; C09K 2211/1011; C09K 2211/1014; C09K 2211/1018
See application file for complete search history.

(56) References Cited

U.S. PATENT DOCUMENTS

| 8,709,613 | B2 * | 4/2014 | Funahashi | ............. | C07C 211/61 |
| | | | | | 428/690 |
| 2005/0236977 | A1 * | 10/2005 | Yamada | ................. | C09K 11/06 |
| | | | | | 585/27 |
| 2007/0252511 | A1 * | 11/2007 | Funahashi | ............. | C07C 211/61 |
| | | | | | 564/426 |
| 2009/0096356 | A1 * | 4/2009 | Murase | .................. | H01L 51/50 |
| | | | | | 313/504 |

(Continued)

FOREIGN PATENT DOCUMENTS

| CN | 107445929 A | * 12/2017 |
| CN | 107445929 A | 12/2017 |

(Continued)

OTHER PUBLICATIONS

S. Kim et al., 160 Synthetic Metals, 1259-1265 (2010) (Year: 2010).*

(Continued)

*Primary Examiner* — Alexander R Pagano
(74) *Attorney, Agent, or Firm* — Mark M. Friedman

(57) ABSTRACT

The present application provides a blue fluorescent material and an OLED display panel, wherein the blue fluorescent material is a tetrahedral structure formed by simultaneously connecting a tert-butyl pyrene and a charge carrier transport unit to a same carbon of cyclohexane; wherein the tert-butyl pyrene increases an external quantum efficiency of the OLED display panel, and the tetrahedral structure increases distance between activated particles and reduces a concentration quenching. The charge carrier transport unit improves a balance of the carrier transfer and alleviates a problem that the current OLED display panel has a low luminous efficiency of the blue light material.

3 Claims, 1 Drawing Sheet

(56) References Cited

U.S. PATENT DOCUMENTS

2015/0299380 A1* 10/2015 Cooper ................. H01G 11/04
429/249
2017/0029362 A1* 2/2017 Howard, Jr. ........ H01L 51/0061
2019/0229277 A1* 7/2019 Hatakeyama ....... H01L 51/0073

FOREIGN PATENT DOCUMENTS

| CN | 110003090 A | * | 7/2019 |
| JP | 2010195708 A | * | 9/2010 |
| KR | 20160056522 A | * | 5/2016 |
| KR | 101837049 B1 | * | 3/2018 |

OTHER PUBLICATIONS

A highly efficient deep blue fluorescent OLED based on diphenylaminofluorenylstyrene-containing emitting materials 高效磷光 OLED 材料的设计、合成与性能研究 Design, Synthesis and Performance of High-Efficiency Phosphorescent OLED Materials.

* cited by examiner

BLUE FLUORESCENT MATERIAL AND DISPLAY PANEL

FIELD OF INVENTION

The present application relates to the field of display, and in particular to a blue fluorescent material and a display panel.

BACKGROUND OF INVENTION

Organic light-emitting diodes (OLEDs) have attracted much attention in academia and industry due to their high contrast ratio, wide viewing angles, low voltage, light-weight, self-illumination, and flexible display panels.

In order to achieve full-color OLED display and high electroluminescence efficiency, excellent color purity and long-life blue light, green light, and red light materials are essential. At present, green light and red light materials have met the requirements of the industry, while blue light materials are far less than the requirements of the industry in regard to efficiency and longevity. Therefore, current OLED display panels have a problem that the luminous efficiency of the blue light material is low, and needs to be solved.

TECHNICAL PROBLEM

The present application provides a blue fluorescent material and a display panel to alleviate the problem that the blue light material in the current OLED display panel has low luminous efficiency.

SUMMARY OF INVENTION

To solve the above problem, the present application provides a blue fluorescent material, wherein the blue fluorescent material is a tetrahedral structure formed by simultaneously connecting a tert-butyl pyrene and a charge carrier transport unit to a same carbon of cyclohexane.

In the present application, the blue fluorescent material has a structural formula of:

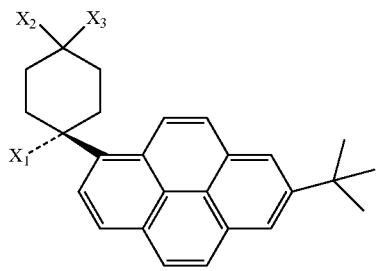

In the blue fluorescent material provided by the present application, $X_1$, $X_2$ and $X_3$ of the structural formula are the same ligand.

In the blue fluorescent material provided by the present application, the $X_1$, the $X_2$, and the $X_3$ each are one of

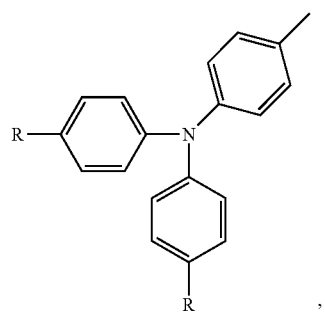

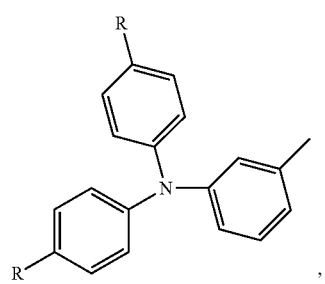

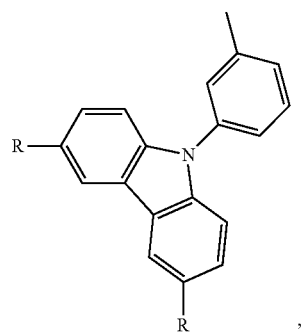

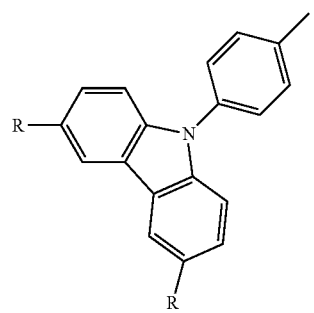

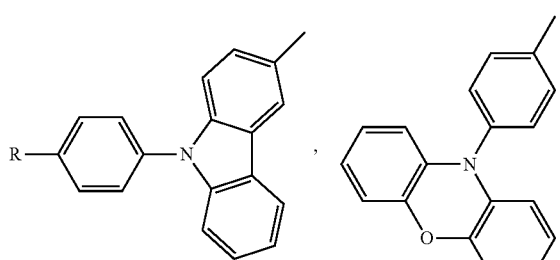

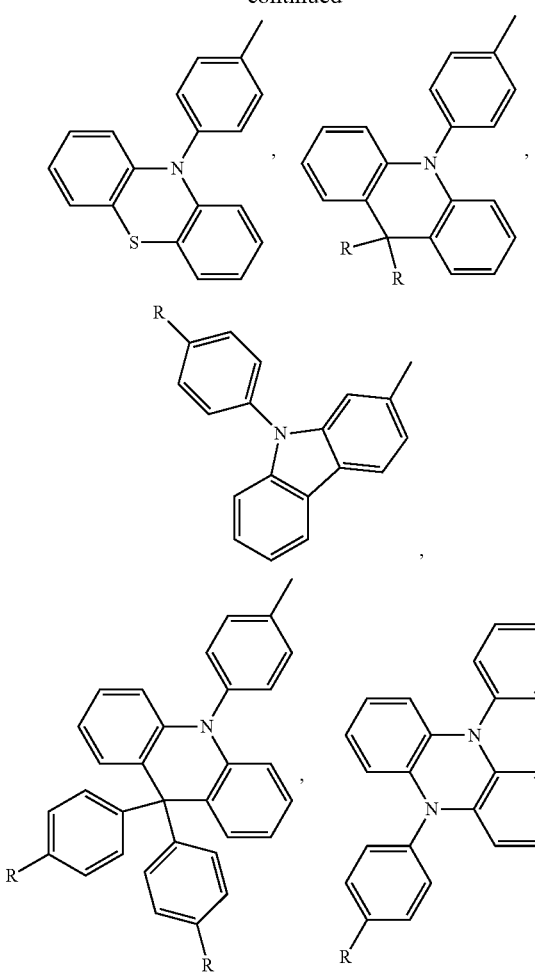

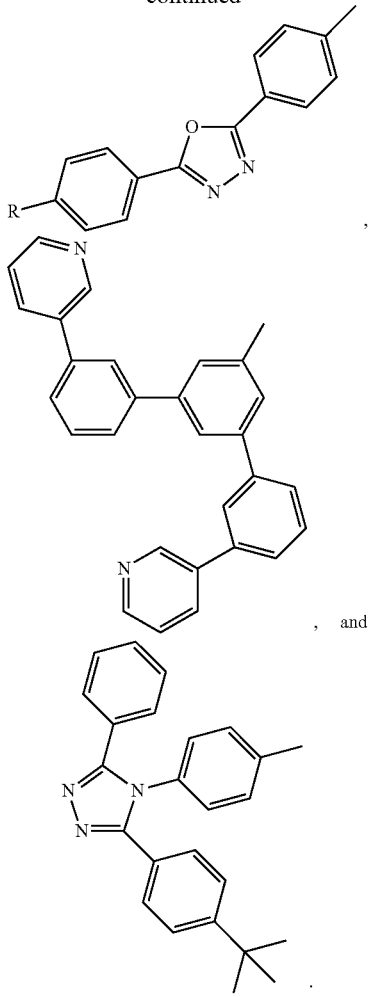

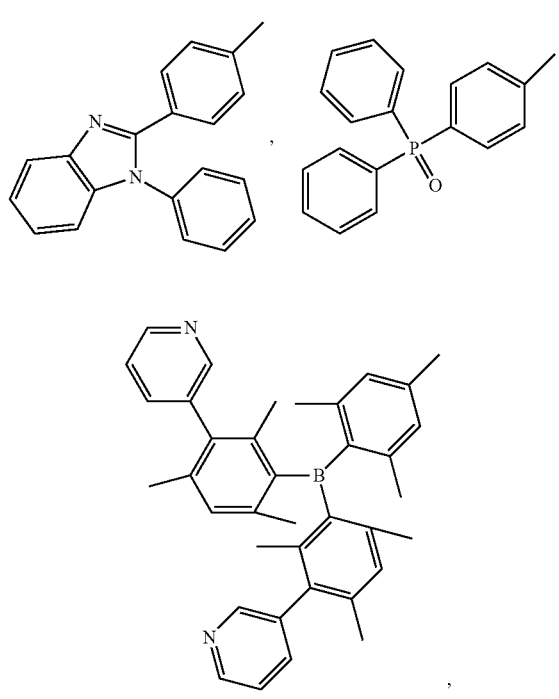

In the blue fluorescent material provided by the present application, at least two of $X_1$, $X_2$, and $X_3$ of the structural formula are different ligands.

In the blue fluorescent material provided by the present application, the $X_1$ and the $X_2$ are the same ligand, and the $X_1$ and the $X_3$ are different ligands.

In the blue fluorescent material provided by the present application, the $X_2$ and the $X_3$ are the same ligand, and the $X_1$ and the $X_2$ are different ligands.

In the blue fluorescent material provided by the present application, the $X_1$, the $X_2$, and the $X_3$ each are one of hydrogen,

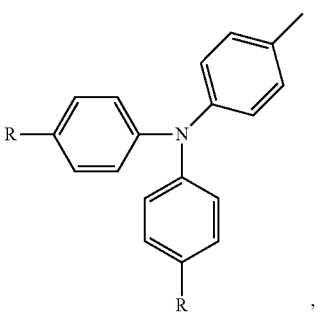

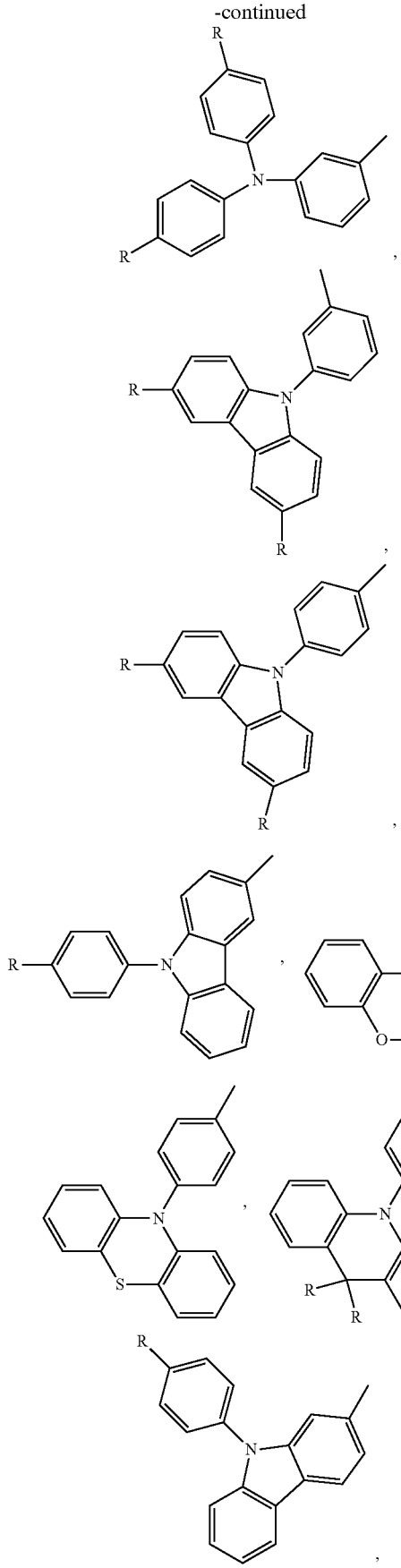
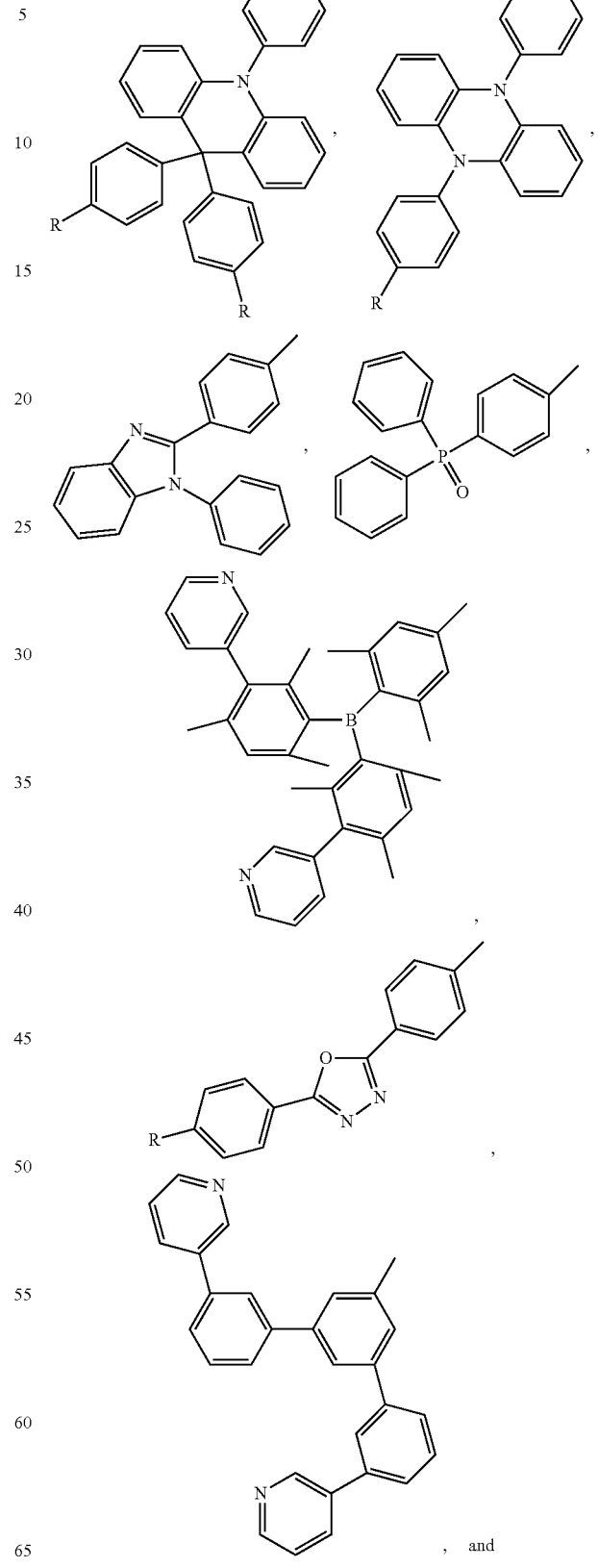

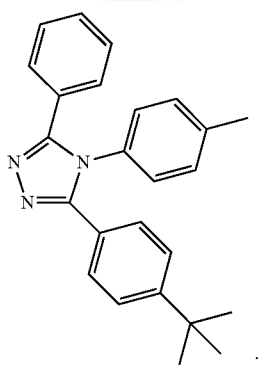
In the blue fluorescent material provided by the present application, the $X_1$, the $X_2$ and the $X_3$ are different ligands.
In the blue fluorescent material provided by the present application, the $X_1$, the $X_2$, and the $X_3$ each are one of hydrogen,
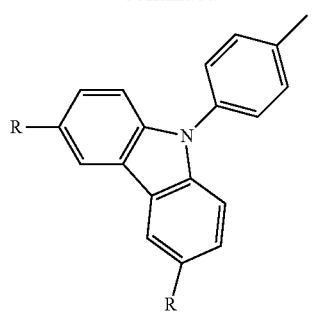,
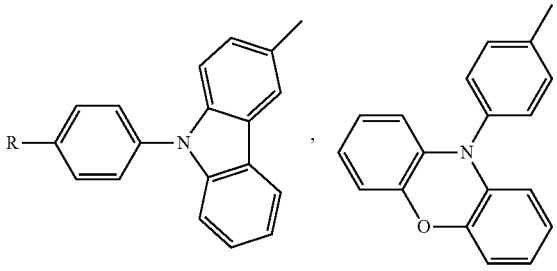,
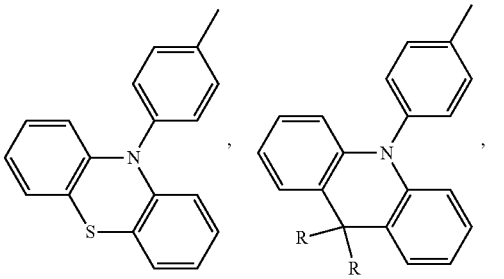,
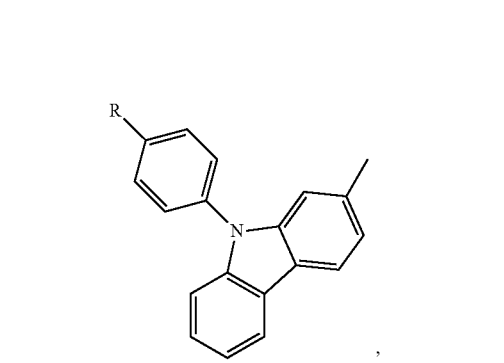,

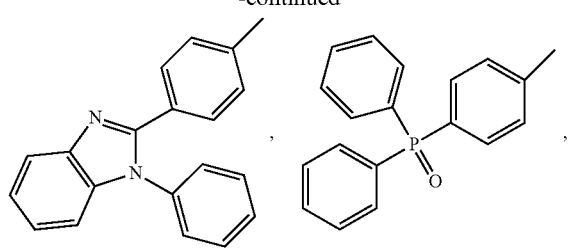
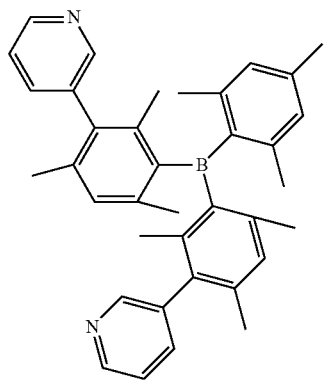
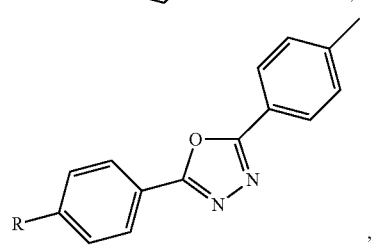
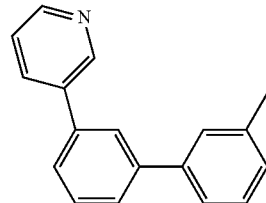
, and
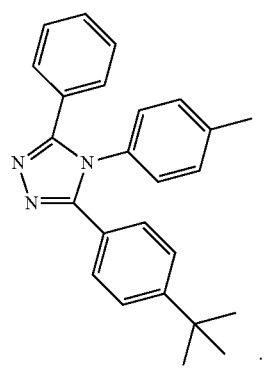
.
In the blue fluorescent material provided by the present application, a R group of any one of:
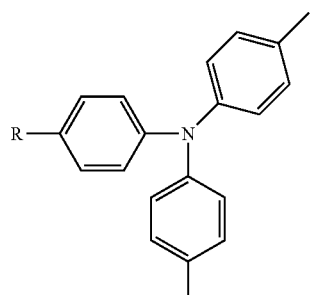
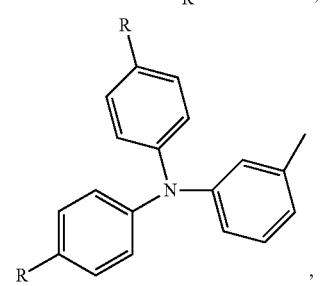
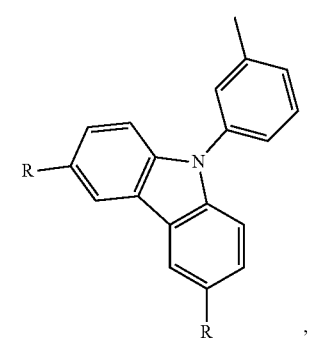
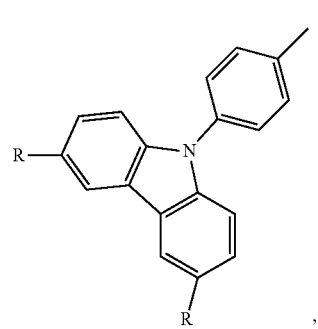
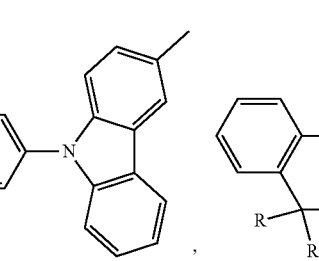

-continued
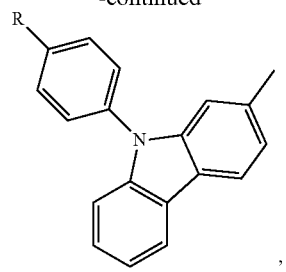
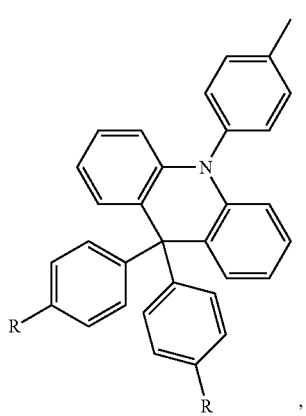
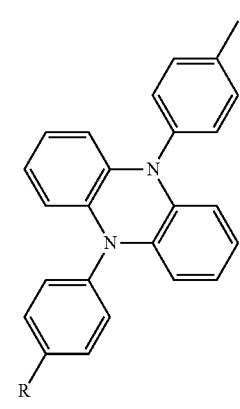
, and
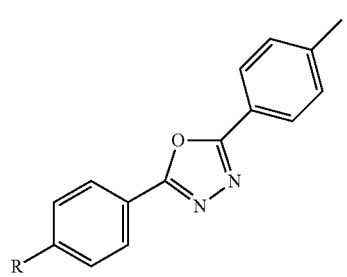
is a C1-C22 alkyl group, or a C1-C22 alkoxy group, or a C1-C22 heteroalkyl group, respectively.
In the blue fluorescent material provided by the present application, a structure of the blue fluorescent material includes:
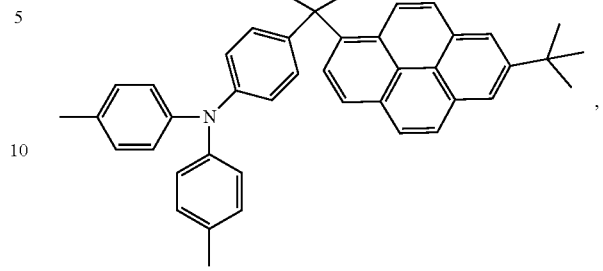
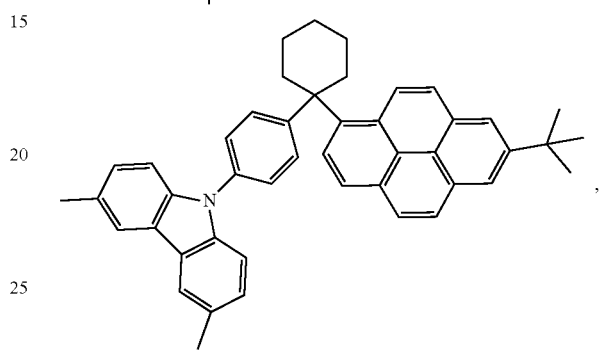
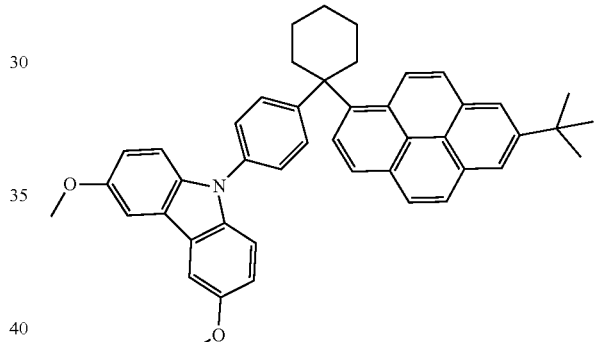
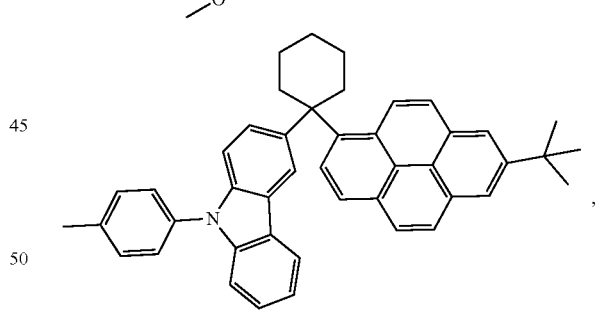
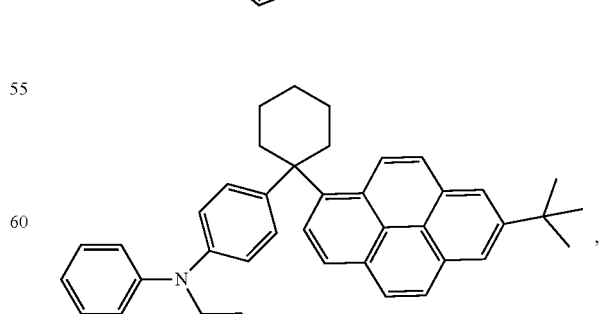

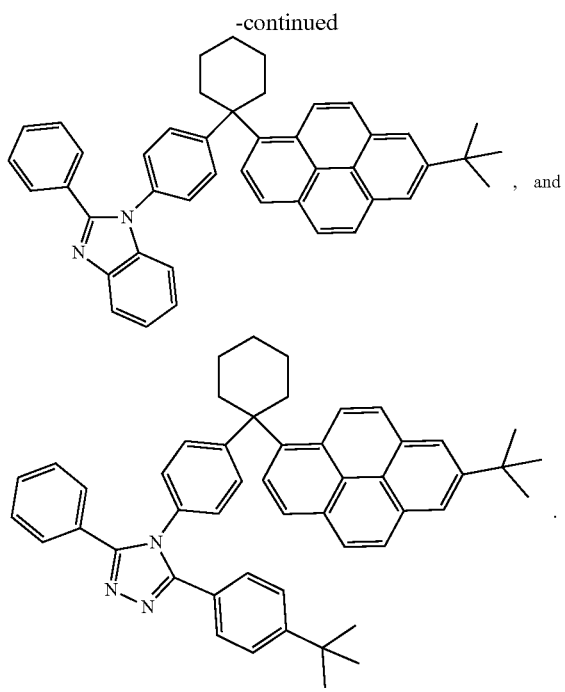

, and

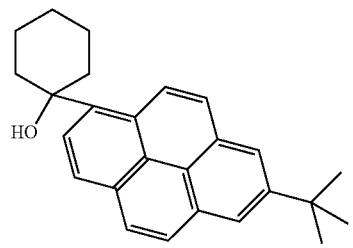

The application also provides a method for preparing a blue fluorescent material, including preparing a precursor and reacting the precursor with a predetermined charge carrier transport unit to obtain a target blue fluorescent molecule.

In the preparation method of the blue fluorescent material provided by the present application, the specific steps of preparing the precursor include: dissolving

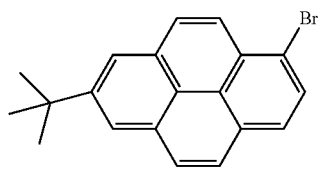

(4 mmol, 1.30 g)

in 100 ml of dehydrogenated and deoxygenated tetrahydrofuran in a single-necked flask to obtain a solution; taking out a small amount of the solution and transferring the solution to a 250 ml of a three-necked flask, adding magnesium (4.4 mmol, 0.11 g) and iodine thereto to obtain a mixed solution and stirring the mixed solution until the mixed solution fades; pouring a remaining portion of the solution into the three-necked flask and stirring the mixed solution for 2 hours to obtain a Grignard reagent; introducing the Grignard reagent into a one-necked flask containing

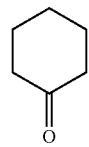

and cyclohexanone (4.4 mmol, 0.43 g) to react for 5 hours to obtain a reaction solution; quenching the reaction solution by adding a little amount of water thereto, then pouring the reaction solution into 100 ml of water, extracting the reaction solution mixed with water with dichloromethane for three times to obtain an organic phase solution, combining the organic phase solution, and then drying, filtering, and vacuum drying the organic phase solution; and separating and purifying the organic phase solution by column chromatography method to obtain

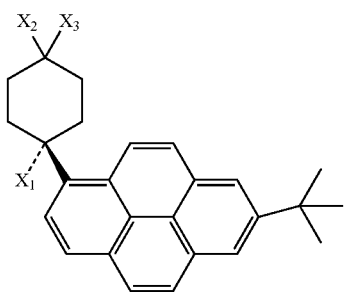

of a pale-yellow precursor powder.

In the preparation method of the blue fluorescent material provided by the present application, the steps of reacting the precursor with the predetermined charge carrier transport unit to obtain the target blue fluorescent molecule includes: taking the precursor (2.2 mmol, 0.78 g), the predetermined charge carrier transport unit (2.0 mmol) and 100 ml of dichloromethane to 250 ml of a two-necked flask, drop wise adding $BF_3 \cdot Et_2O$ solution (2.2 mmol, 0.3 ml) into the two-necked flask under $Ar_2$, and stirring for 24 hours to obtain a reaction solution; quenching the reaction solution by adding a little amount of water thereto, then pouring the reaction solution into 100 ml of water, extracting the reaction solution mixed with water with dichloromethane for three times to obtain organic phase solution, combining the organic phase solution, and then drying, filtering, and vacuum drying the organic phase solution; and separating and purifying the organic phase solution by column chromatography method to obtain a target blue fluorescent molecule.

The application also provides an organic light-emitting diode (OLED) display panel, including: a substrate; and a pixel electrode layer, a hole transport layer, a hole injection layer, a luminescent material layer, an electron injection layer, an electron transport layer, and a common electrode layer sequentially disposed on the substrate; wherein the luminescent material layer includes a red light material layer, a green light material layer, and a blue light material layer; the blue light material layer is a tetrahedral structure formed by simultaneously connecting a tert-butyl pyrene and a charge carrier transport unit to a same carbon of cyclohexane.

In the OLED display panel provided by the present application, the blue fluorescent material has a structural formula of:

In the OLED display panel provided by the present application, $X_1$, $X_2$ and $X_3$ of the structural formula are the same ligand.

In the OLED display panel provided by the present application, at least two of $X_1$, $X_2$, and $X_3$ of the structural formula are different ligands.

BENEFICIAL EFFECT

The present application provides a blue fluorescent material and an OLED display panel, wherein the blue fluorescent material is a tetrahedral structure formed by simultaneously connecting a tert-butyl pyrene and a charge carrier transport unit to a same carbon of cyclohexane; wherein the tert-butyl pyrene increases an external quantum efficiency of the OLED display, and the tetrahedral structure increases distance between activated particles and reduces a risk of concentration quenching and greatly increases membrane fluorescence quantum efficiency. In addition, the transport unit with high charge carrier mobility can improve a balance of the charge carrier transport, increase a probability of recombination, further improve an external quantum efficiency of an OLED display device, and alleviate the problem of low luminous efficiency of current OLED display panel.

DESCRIPTION OF DRAWINGS

In order to more clearly illustrate the technical solutions in the embodiments of the present invention, the following figures described in the embodiments will be briefly introduced. It is obvious that the drawings described below are merely some embodiments of the present invention, other drawings can also be obtained by the person ordinary skilled in the field based on these drawings without doing any creative activity.

EMBODIMENTS

Figure 1:
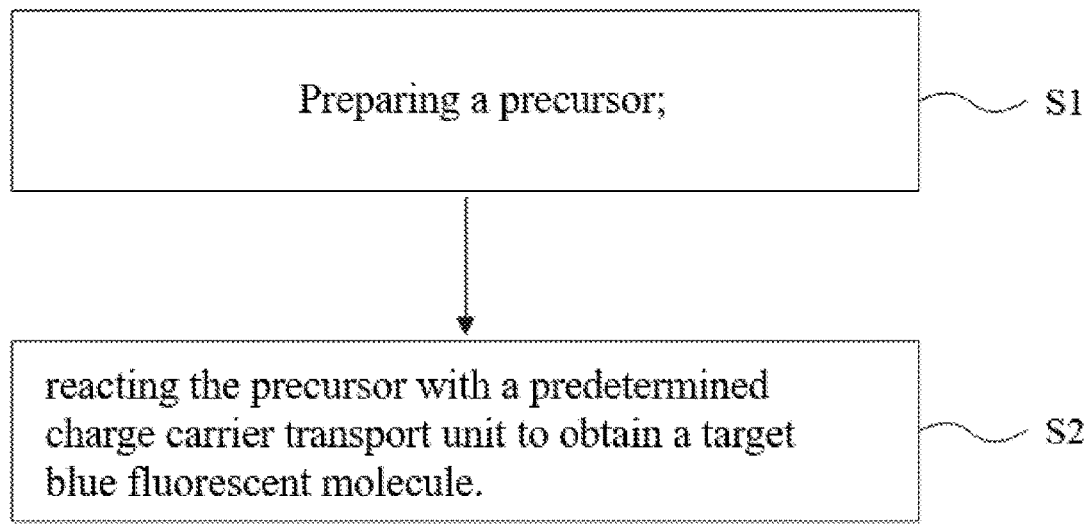
FIG. 1 is a flowchart of preparing a blue fluorescent material according to an embodiment of the present application.

The following description of the embodiments is provided to illustrate the specific embodiments of the invention. Directional terminology mentioned in the application, such as "above", "under", "front", "back", "left", "right", "inside", "outside", "side", etc., are only refer to the directions of the accompanying drawings. Therefore, the directional terminology used is for illustrating and understanding the application and is not intended to limit the application. In the figures, structurally similar elements are denoted by the same reference numerals.

OLED display device utilizes electroluminescence of electrons and holes in a luminescent material layer to display so that materials of the luminescent material layer play a critical role in the display of OLED display device, and high luminous efficiency is an important prerequisite for a practical application of such materials. One of the most effective ways to increase luminous efficiency is to increase a doping concentration of activated ions. The pyrene blue light molecule with a rigid planar structure can achieve external quantum efficiency of 11% through triplet-triplet fusion (traditional singlet blue fluorescent material does not exceed 5%). However, its tight π-π stacking causes a concentration quenching effect, that is, a large amount of non-radiation relaxation and reverse energy transmission, resulting in a significant decrease in luminous intensity and efficiency.

In view of a problem that the blue light material of the current OLED display panel has low luminous efficiency, the present application provides a blue fluorescent material to alleviate the problem.

In one embodiment, the present application provides a blue fluorescent material, which is a tetrahedral structure having a structural formula of

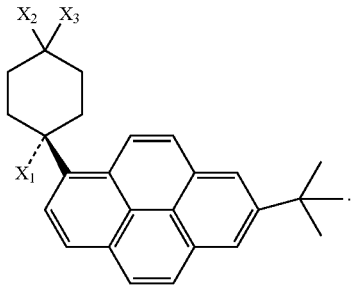

The embodiment of the present application provides a blue fluorescent material, which is a tetrahedral structure formed by simultaneously connecting a tert-butyl pyrene and a charge carrier transport unit to a same carbon of cyclohexane, the tert-butyl pyrene increases an external quantum efficiency of the OLED display panel. The tetrahedral structure increases distance between activated particles and reduces the concentration quenching. In addition, the transport unit with high charge carrier mobility improves a balance of the charge carrier transport, increases a probability of recombination, further improves an external quantum efficiency of an OLED display device, and alleviates a problem of low luminous efficiency of the current OLED display panel.

Different ligands will produce blue fluorescent materials with different structures. Different charge carrier transport unit that shares a carbon with tert-butyl pyrene and a different number of the charge carrier transport units will obtain different blue fluorescent materials. Specific structural formulas of the blue fluorescent material will be described in detail below by the embodiments.

In one embodiment, $X_1$, $X_2$ and $X_3$ is the same ligand selected from:

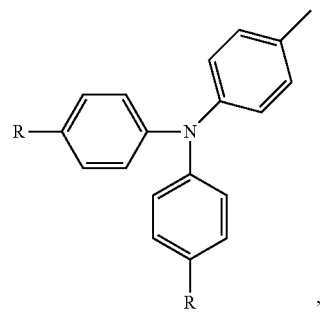

,

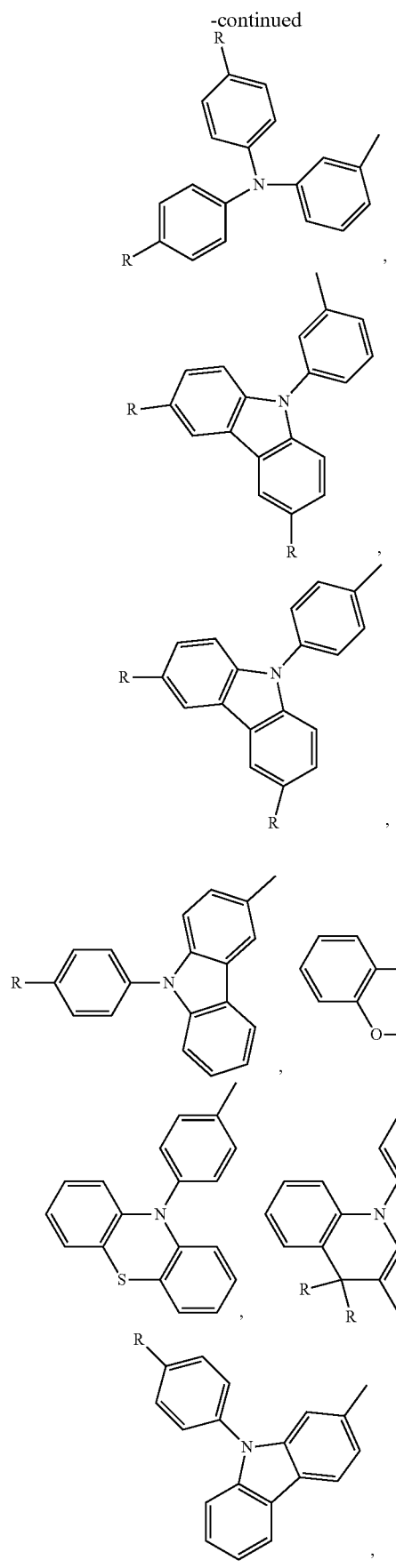
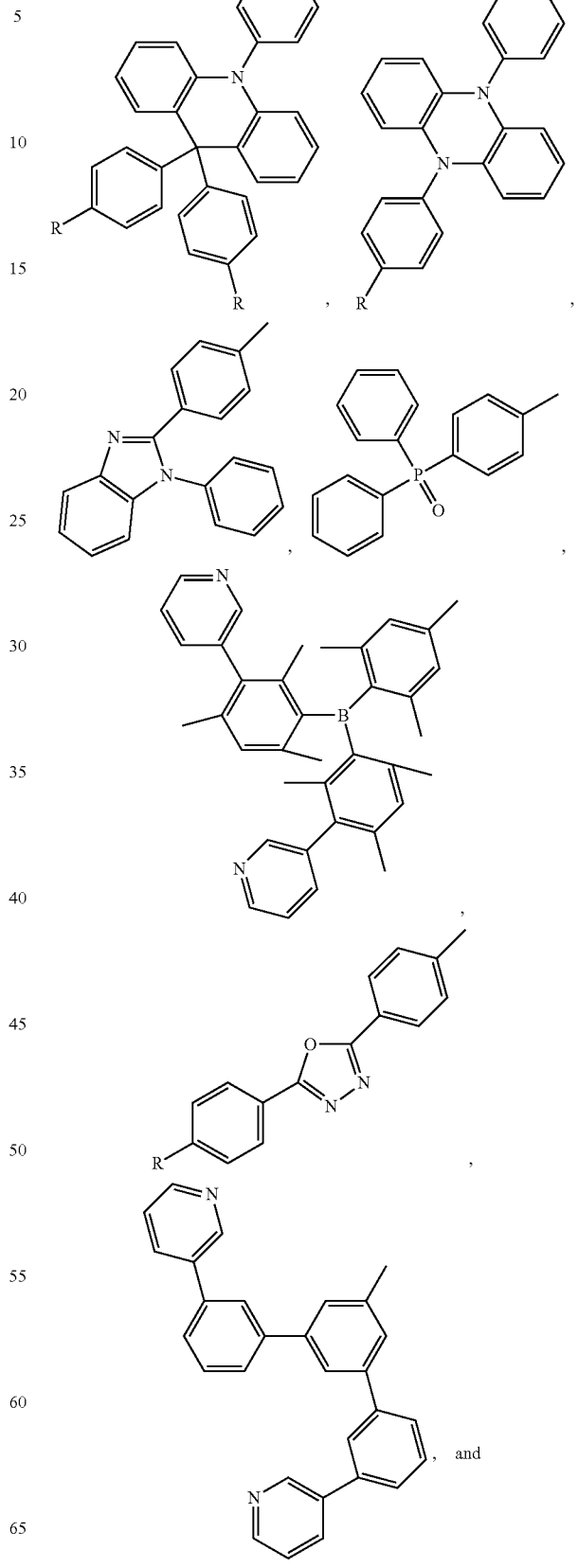

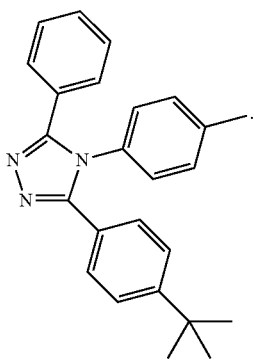
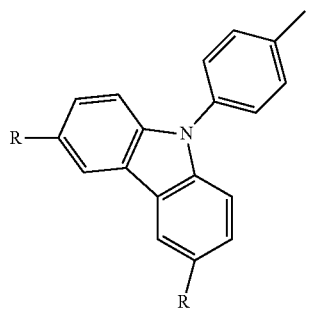
In another embodiment, $X_1$ and $X_2$ are the same ligands, and the $X_1$ and the $X_3$ are different ligands; or the $X_2$ and the $X_3$ are the same ligand, and the $X_1$ and the $X_2$ are different ligands, they are selected from: hydrogen,
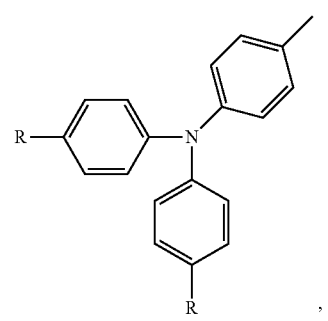
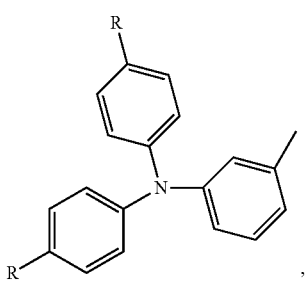
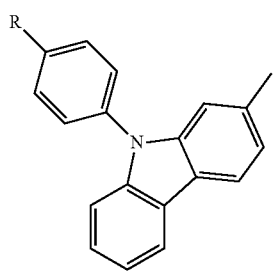
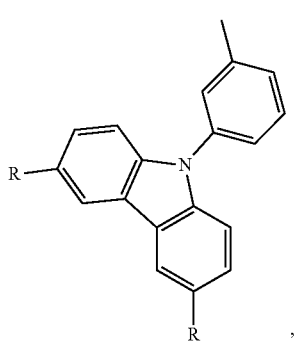
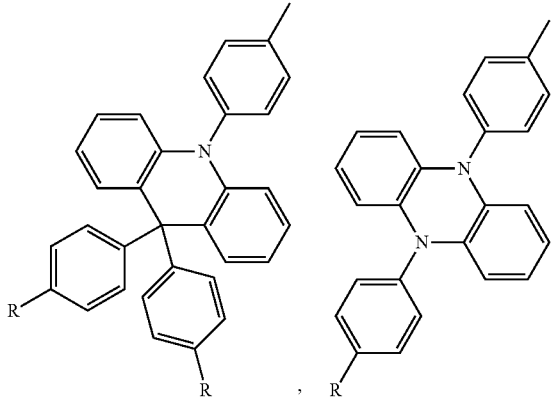

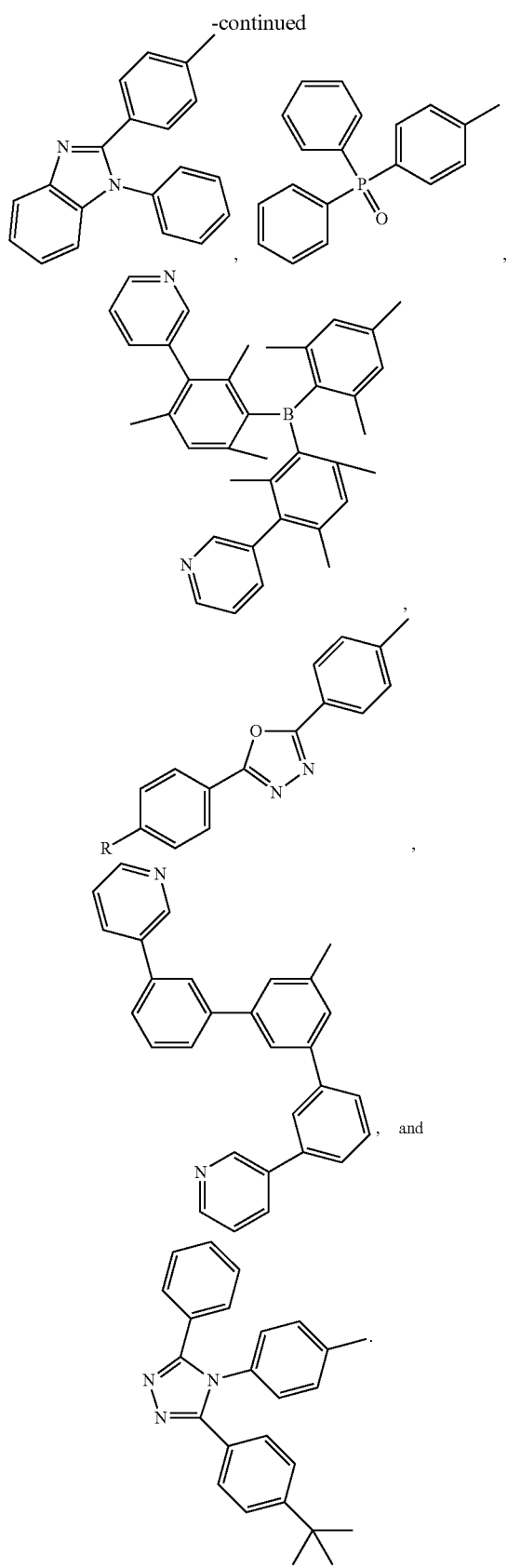
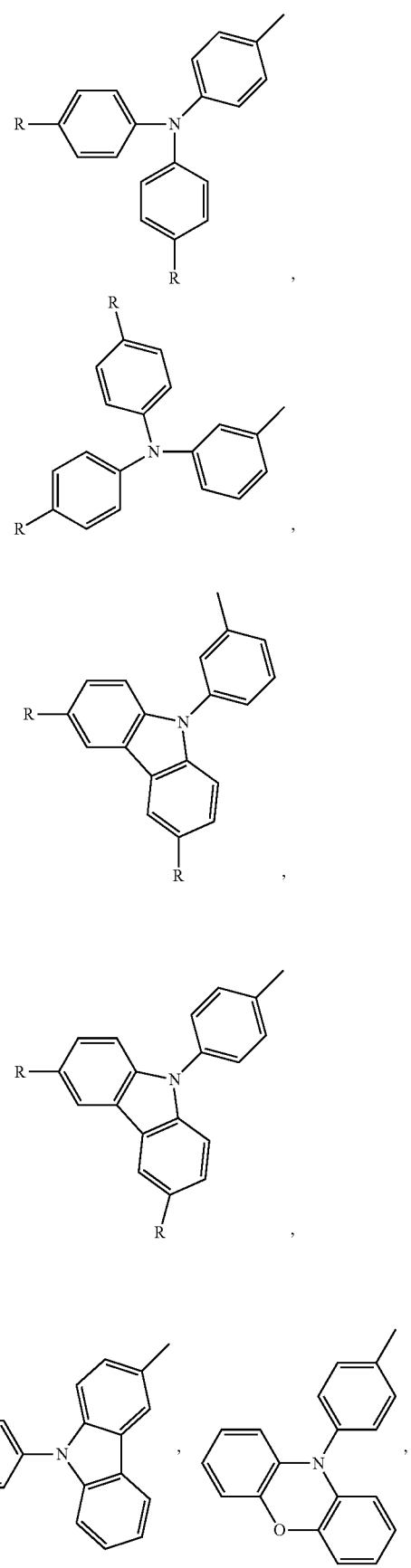
In another embodiment, the $X_1$, the $X_2$, and the $X_3$ are different ligands, they are selected from: hydrogen,

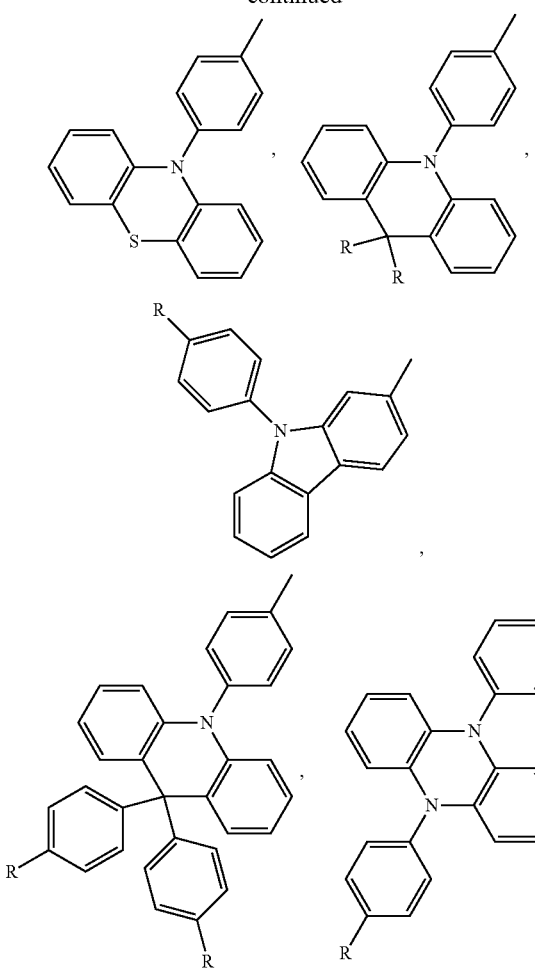
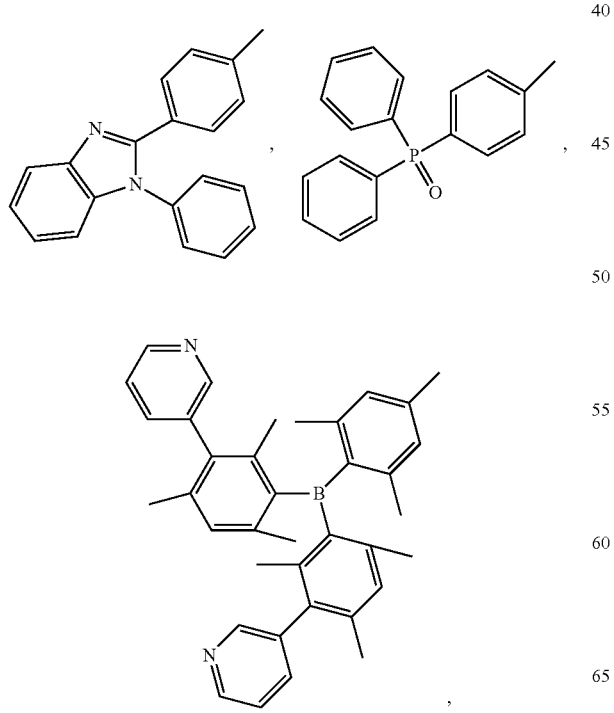
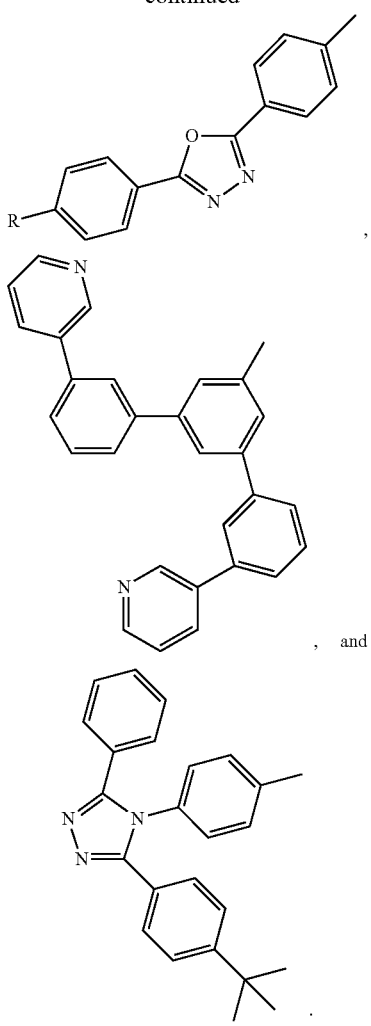
, and
In the above embodiments, a R group of any one of

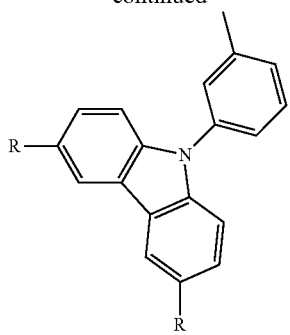,
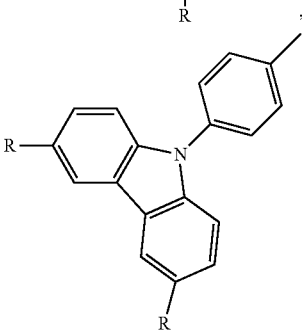,
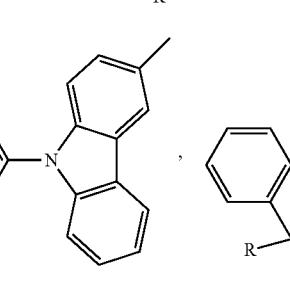,
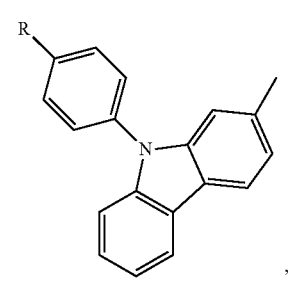,
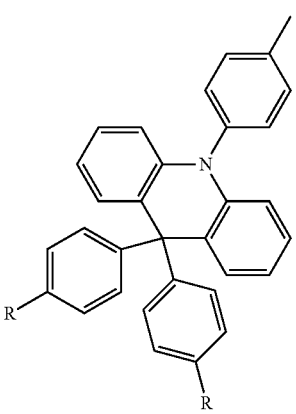,
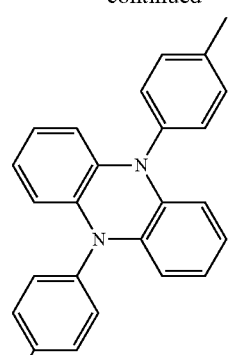, and
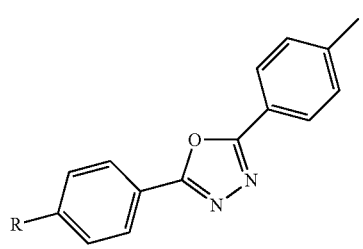
is a C1-C22 alkyl group, or a C1-C22 alkoxy group, or a C1-C22 heteroalkyl group, respectively.
Specific structures of
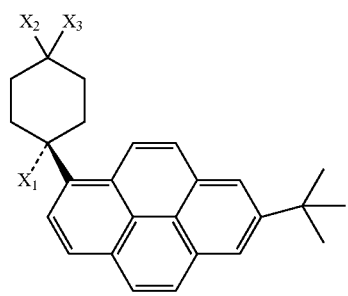
include:
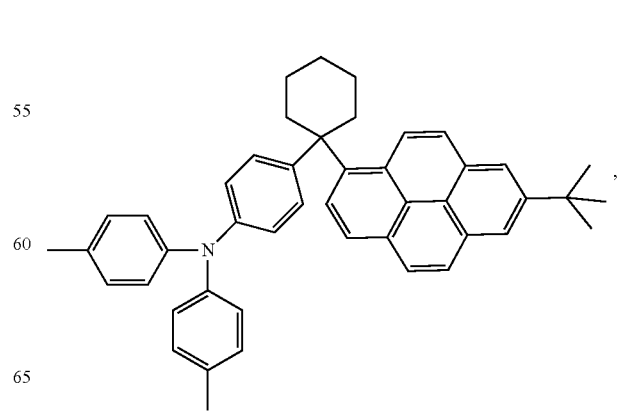,

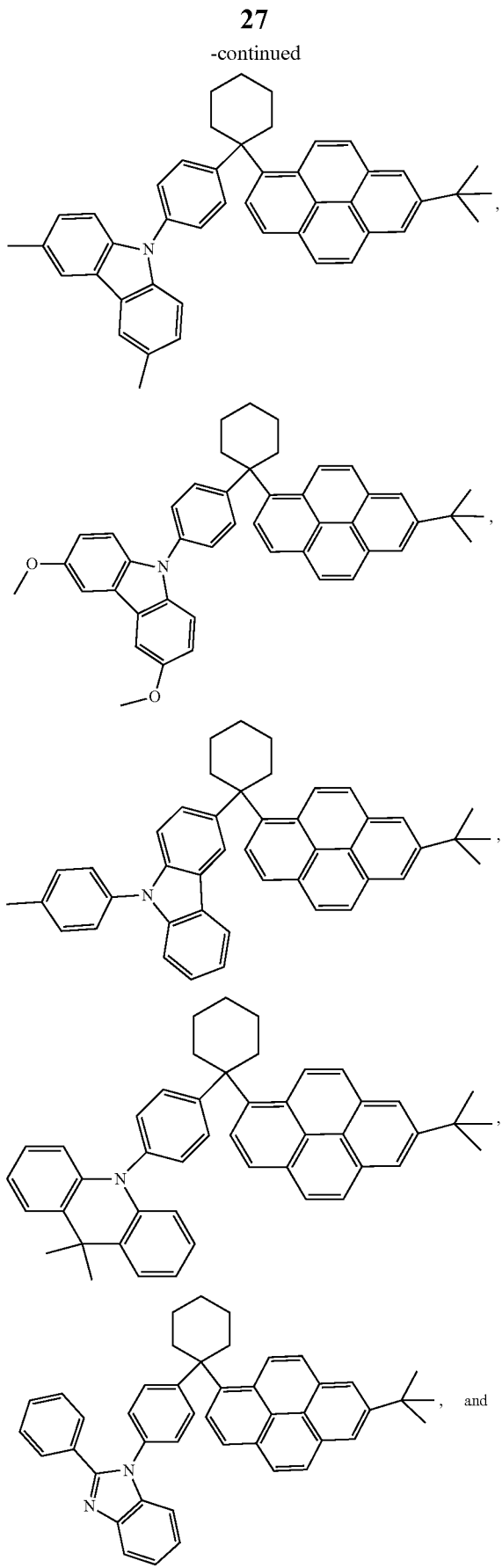

,

,

,

, and

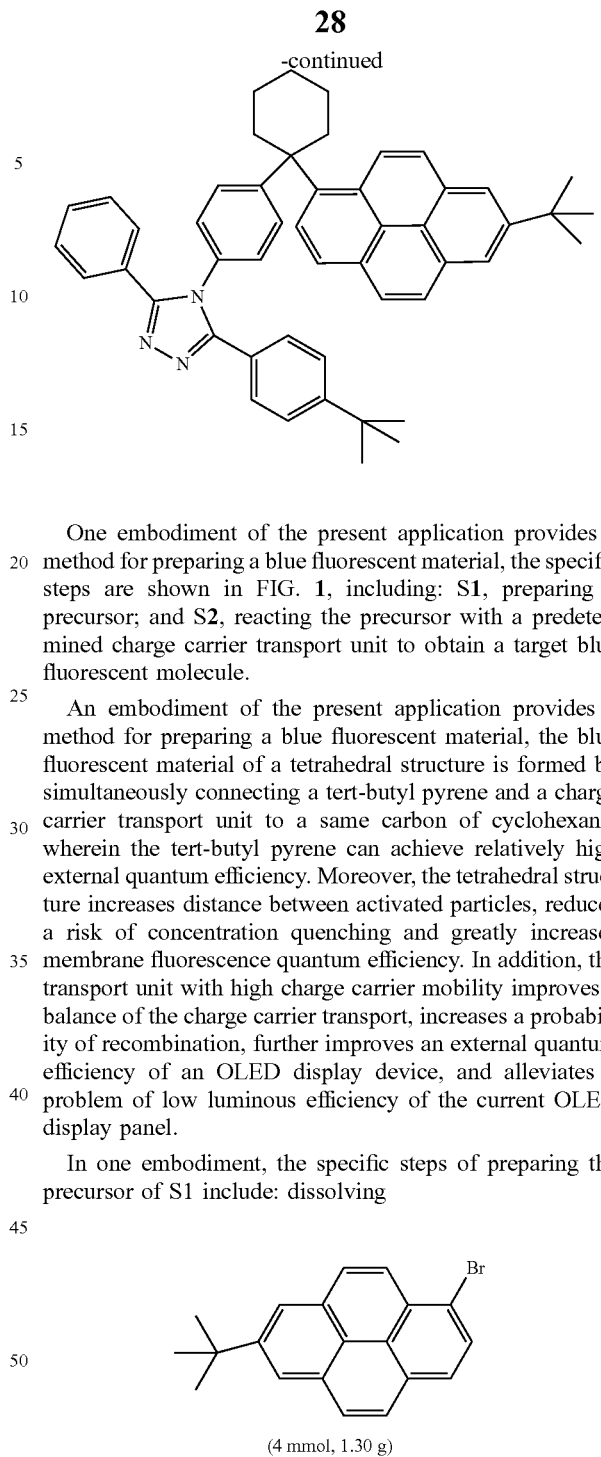

,

One embodiment of the present application provides a method for preparing a blue fluorescent material, the specific steps are shown in FIG. 1, including: S1, preparing a precursor; and S2, reacting the precursor with a predetermined charge carrier transport unit to obtain a target blue fluorescent molecule.

An embodiment of the present application provides a method for preparing a blue fluorescent material, the blue fluorescent material of a tetrahedral structure is formed by simultaneously connecting a tert-butyl pyrene and a charge carrier transport unit to a same carbon of cyclohexane; wherein the tert-butyl pyrene can achieve relatively high external quantum efficiency. Moreover, the tetrahedral structure increases distance between activated particles, reduces a risk of concentration quenching and greatly increases membrane fluorescence quantum efficiency. In addition, the transport unit with high charge carrier mobility improves a balance of the charge carrier transport, increases a probability of recombination, further improves an external quantum efficiency of an OLED display device, and alleviates a problem of low luminous efficiency of the current OLED display panel.

In one embodiment, the specific steps of preparing the precursor of S1 include: dissolving (4 mmol, 1.30 g)

in 100 ml of dehydrogenated and deoxygenated tetrahydrofuran in a single-necked flask to obtain a solution; taking out a small amount of the solution and transferring the solution to a 250 ml three-necked flask, adding magnesium (4.4 mmol, 0.11 g) and iodine thereto to obtain a mixed solution and stirring the mixed solution until a color of the mixed solution fades; pouring a remaining portion of the solution into the three-necked flask and stirring the mixed solution for 2 hours to obtain a Grignard reagent; introducing the Grignard reagent into a one-necked flask containing

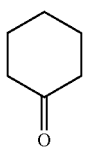

and cyclohexanone (4.4 mmol, 0.43 g) to react for 5 hours to obtain a reaction solution; quenching the reaction solution by adding a little amount of water thereto, then pouring the reaction solution into 100 ml of water, extracting the reaction solution mixed with water with dichloromethane for three times to obtain an organic phase solution, combining the organic phase solution, and then drying, filtering, and vacuum drying the organic phase solution; and separating and purifying the organic phase solution by column chromatography method to obtain of a pale-yellow precursor powder.

In the embodiment, the synthetic route of the precursor is:

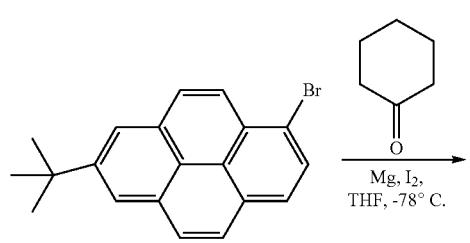

In one embodiment, a target structure of the blue fluorescent material is

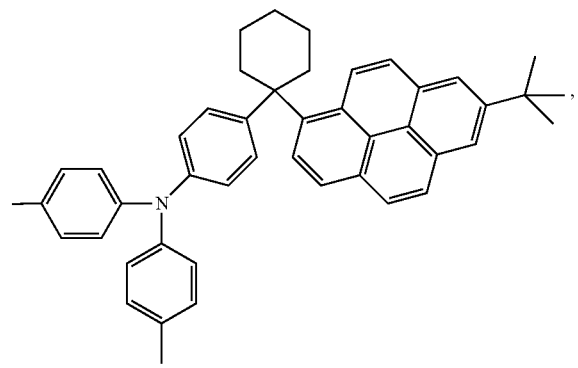 [SMILES: Cc1ccc(N(c2ccc(C)cc2)c2ccc(C3(c4ccc5ccc6cc(C(C)(C)C)cc7ccc4c5c67)CCCCC3)cc2)cc1]

the specific steps S2 of reacting the precursor with the charge carrier transport unit include: taking (2.2 mmol, 0.78 g)

(2.0 mmol, 0.55 g)

and 100 ml of dichloromethane to a 250 ml two-necked flask, adding $BF_3 \cdot Et_2O$ (2.2 mmol, 0.3 ml) dropwise thereto under an $Ar_2$ atmosphere and stirring for 24 hours.

Quenching the reaction solution by adding a little amount of water, then pouring the reaction solution into a water of 100 ml, extracting for three times with dichloromethane, and performing processes of organic phases combining, drying, filtering, and vacuum drying.

Performing isolation and purification by column chromatography to obtain a white powder

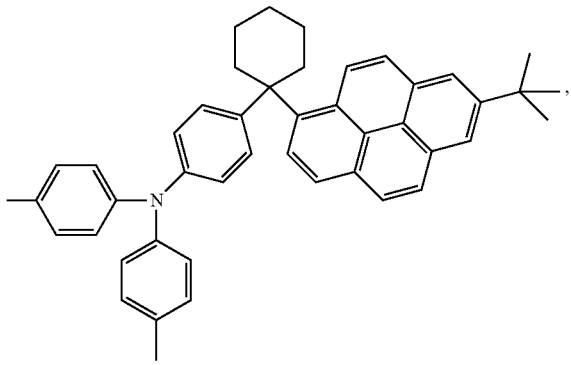 [SMILES: Cc1ccc(N(c2ccc(C)cc2)c2ccc(C3(c4ccc5ccc6cc(C(C)(C)C)cc7ccc4c5c67)CCCCC3)cc2)cc1]

10.87 g, yield 71%.

In the embodiment, the synthetic route of

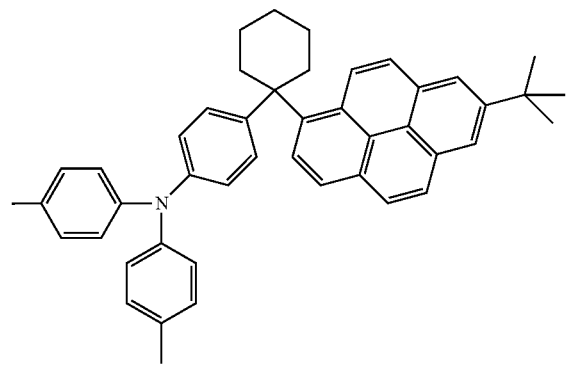 [SMILES: Cc1ccc(N(c2ccc(C)cc2)c2ccc(C3(c4ccc5ccc6cc(C(C)(C)C)cc7ccc4c5c67)CCCCC3)cc2)cc1]

is:

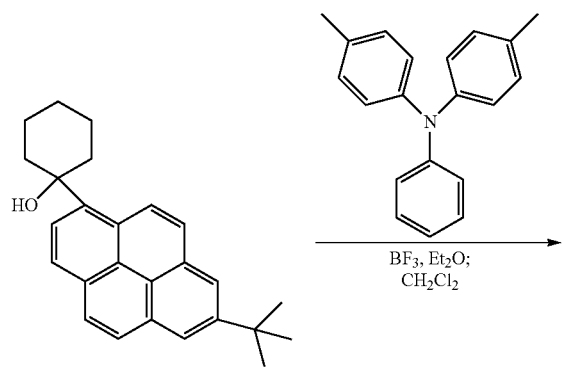

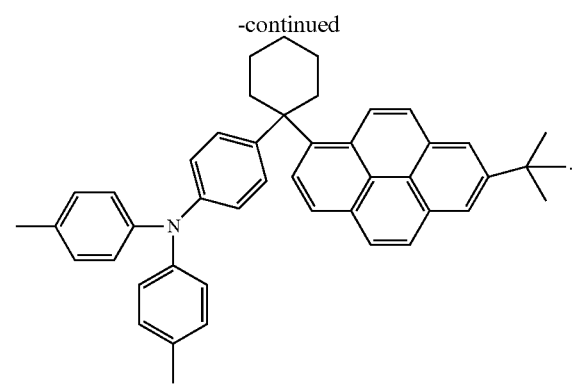

In one embodiment, the target structure of the blue fluorescent material is

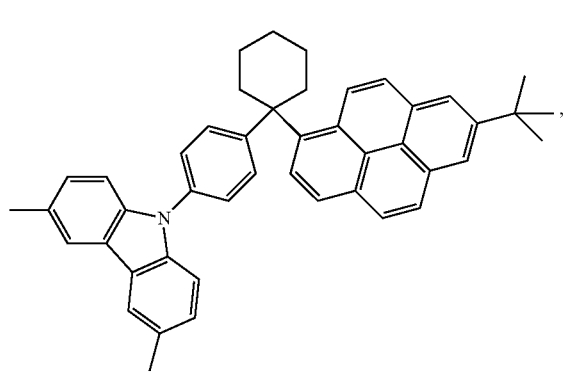 [SMILES: Cc1ccc2c(c1)c1cc(C)ccc1n2-c1ccc(C2(c3ccc4ccc5cc(C(C)(C)C)cc6ccc3c4c56)CCCCC2)cc1]

the specific steps S2 of reacting the precursor with the charge carrier transport unit include: taking

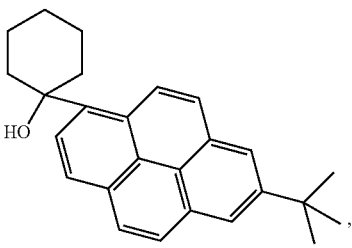

(2.2 mmol, 0.78 g)

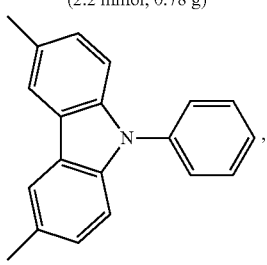

(2.0 mmol, 0.54 g)

and 100 ml of dichloromethane to a two-necked flask of 250 ml, adding $BF_3.Et_2O$ (2.2 mmol, 0.3 ml) dropwise thereto under an $Ar_2$ atmosphere and stirring for 24 hours.

Quenching the reaction solution by adding a little amount of water, then pouring the reaction solution into a water of 100 ml, extracting for three times with dichloromethane, and performing processes of organic phases combining, drying, filtering, and vacuum drying.

Performing isolation and purification by column chromatography to obtain a white powder

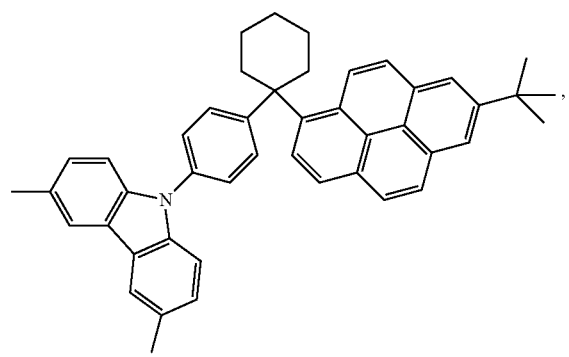 [SMILES: Cc1ccc2c(c1)c1cc(C)ccc1n2-c1ccc(C2(c3ccc4ccc5cc(C(C)(C)C)cc6ccc3c4c56)CCCCC2)cc1]

20.91 g, yield 75%.

In the embodiment, the synthetic route of

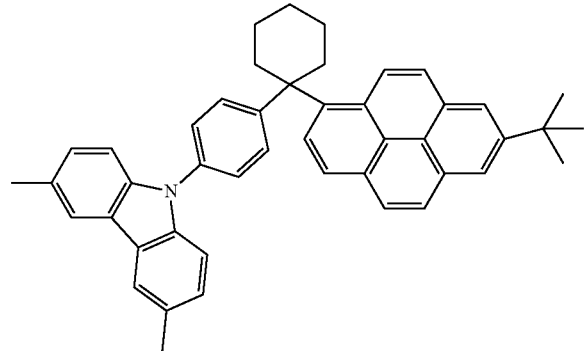 [SMILES: Cc1ccc2c(c1)c1cc(C)ccc1n2-c1ccc(C2(c3ccc4ccc5cc(C(C)(C)C)cc6ccc3c4c56)CCCCC2)cc1]

is:

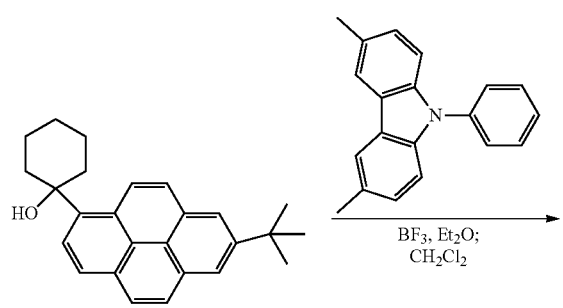

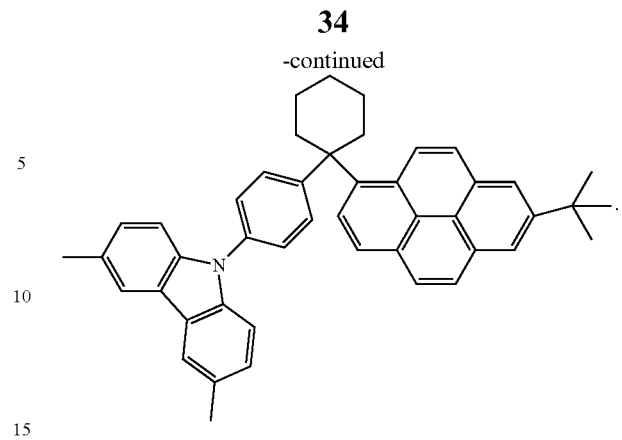

In one embodiment, the target structure of the blue fluorescent material is

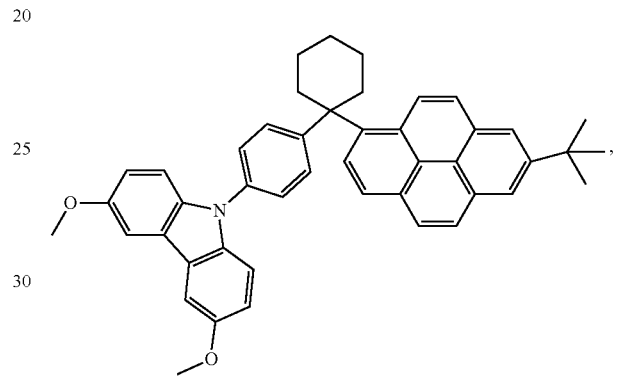

the specific steps S2 of reacting the precursor with the charge carrier transport unit include: taking

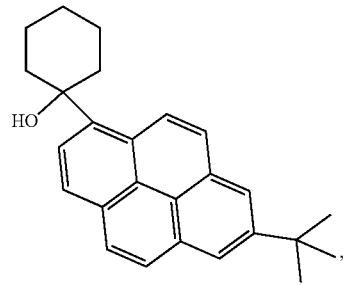

(2.2 mmol, 0.78 g)

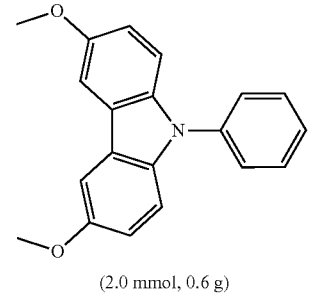

(2.0 mmol, 0.6 g)

and 100 ml of dichloromethane to a 250 ml two-necked flask, adding $BF_3 \cdot Et_2O$ (2.2 mmol, 0.3 ml) dropwise thereto under an $Ar_2$ atmosphere and stirring for 24 hours.

Quenching the reaction solution by adding a little amount of water, then pouring the reaction solution into a water of 100 ml, extracting for three times with dichloromethane, and performing processes of organic phases combining, drying, filtering, and vacuum drying.

Performing isolation and purification by column chromatography to obtain a white powder

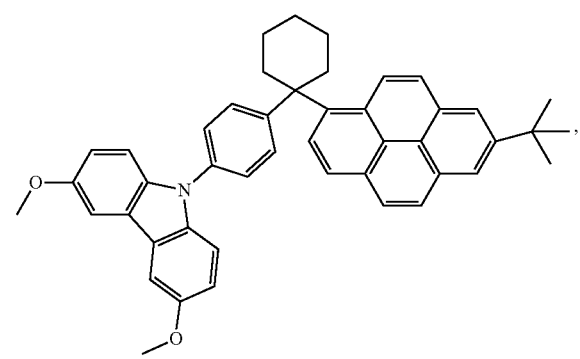 [SMILES: COc1ccc2c(c1)c1cc(OC)ccc1n2-c1ccc(C2(c3ccc4ccc5cc(C(C)(C)C)cc6ccc3c4c56)CCCCC2)cc1]

31 g, yield 78%.

In the embodiment, the synthetic route of

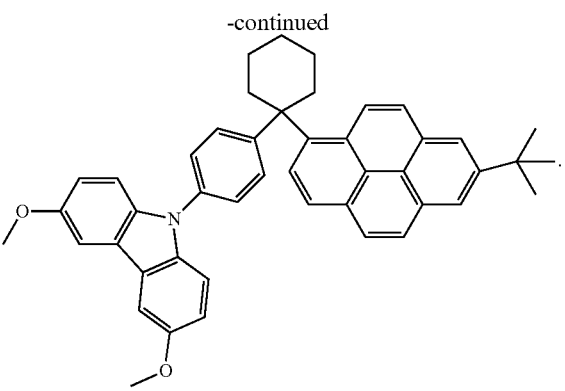

-continued

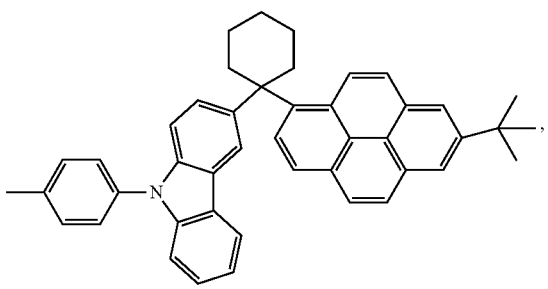

In one embodiment, the target structure of the blue fluorescent material is

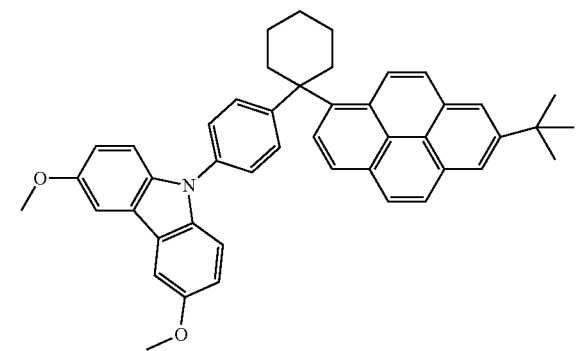 [SMILES: COc1ccc2c(c1)c1cc(OC)ccc1n2-c1ccc(C2(c3ccc4ccc5cc(C(C)(C)C)cc6ccc3c4c56)CCCCC2)cc1]

the specific steps S2 of reacting the precursor with the charge carrier transport unit include: taking

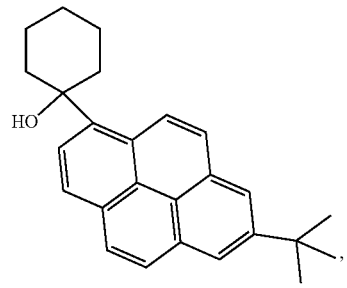

(2.2 mmol, 0.78 g)

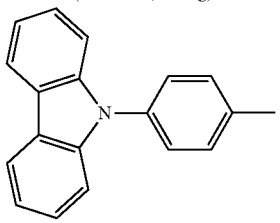

(2.0 mmol, 0.51 g)

and 100 ml of dichloromethane to a 250 ml two-necked flask, adding $BF_3 \cdot Et_2O$ (2.2 mmol, 0.3 ml) dropwise thereto under an $Ar_2$ atmosphere and stirring for 24 hours.

Quenching the reaction solution by adding a little amount of water, then pouring the reaction solution into a water of 100 ml, extracting for three times with dichloromethane, and performing processes of organic phases combining, drying, filtering, and vacuum drying.

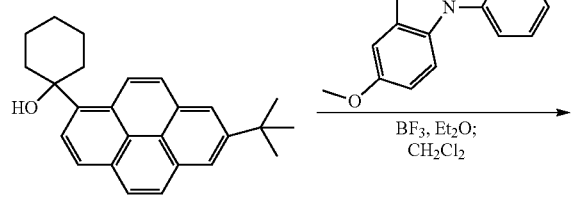

Performing isolation and purification by column chromatography to obtain a white powder

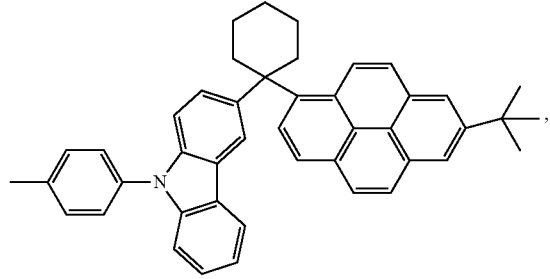 [SMILES: Cc1ccc(-n2c3ccccc3c3cc(C4(c5ccc6ccc7cc(C(C)(C)C)cc8ccc5c6c78)CCCCC4)ccc32)cc1]

40.89 g, yield 75%.

In the embodiment, the synthetic route of

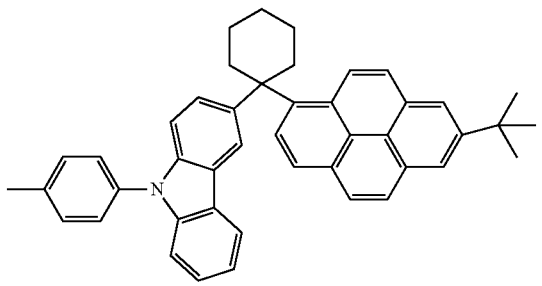 [SMILES: Cc1ccc(-n2c3ccccc3c3cc(C4(c5ccc6ccc7cc(C(C)(C)C)cc8ccc5c6c78)CCCCC4)ccc32)cc1]

is:

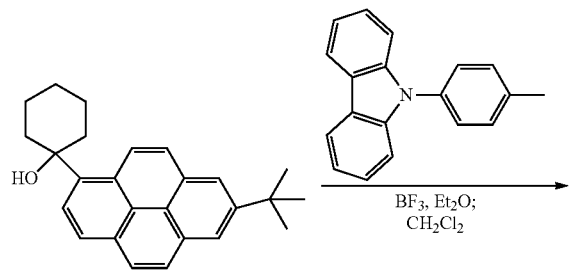

In one embodiment, the target structure of the blue fluorescent material is

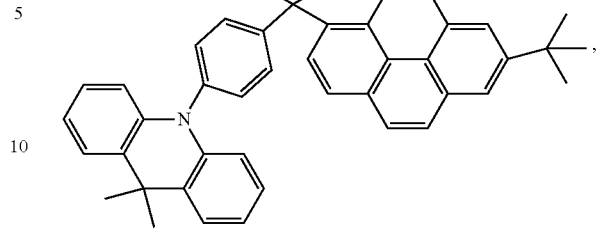

the specific steps S2 of reacting the precursor with the charge carrier transport unit include: taking

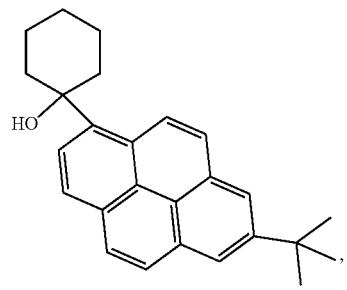

(2.2 mmol, 0.78 g)

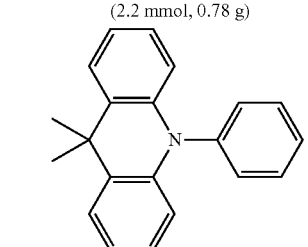

(2.0 mmol, 0.57 g)

and 100 ml of dichloromethane to a 250 ml two-necked flask, adding $BF_3 \cdot Et_2O$ (2.2 mmol, 0.3 ml) dropwise thereto under an $Ar_2$ atmosphere and stirring for 24 hours.

Quenching the reaction solution by adding a little amount of water, then pouring the reaction solution into a water of 100 ml, extracting for three times with dichloromethane, and performing processes of organic phases combining, drying, filtering, and vacuum drying.

Performing isolation and purification by column chromatography to obtain a white powder

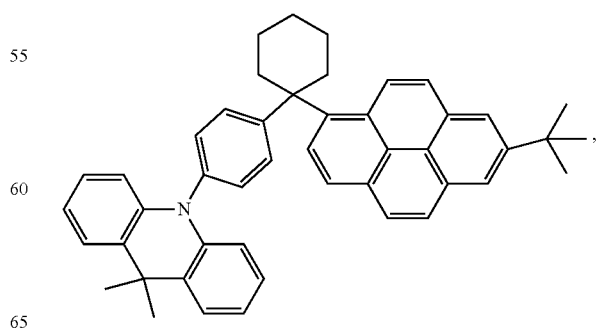

50.79 g, yield 63%.

In the embodiment, the synthetic route of

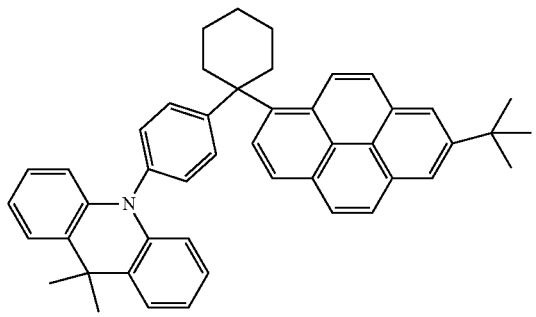 [SMILES: CC(C)(C)c1cc2ccc3ccc(C4(c5ccc(N6c7ccccc7C(C)(C)c7ccccc76)cc5)CCCCC4)c4ccc(c1)c2c34]

is:

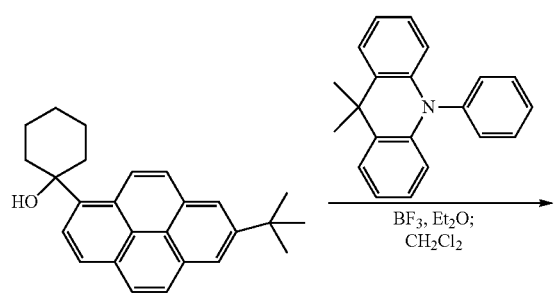

In one embodiment, the target structure of the blue fluorescent material is

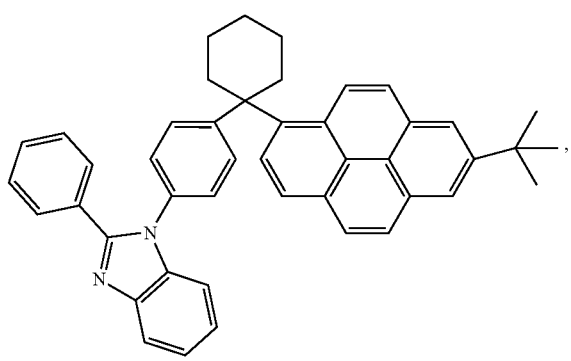 [SMILES: CC(C)(C)c1cc2ccc3ccc(C4(c5ccc(-n6c(-c7ccccc7)nc7ccccc76)cc5)CCCCC4)c4ccc(c1)c2c34]

the specific steps S2 of reacting the precursor with the charge carrier transport unit include: taking

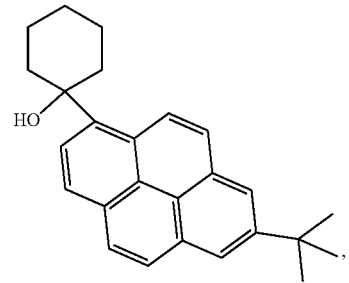

(2.2 mmol, 0.78 g)

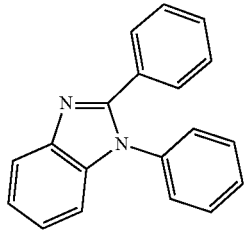

(2.0 mmol, 0.54 g)

and 100 ml of dichloromethane to a two-necked flask of 250 ml, adding $BF_3 \cdot Et_2O$ (2.2 mmol, 0.3 ml) dropwise thereto under an $Ar_2$ atmosphere and stirring for 24 hours.

Quenching the reaction solution by adding a little amount of water, then pouring the reaction solution into a water of 100 ml, extracting for three times with dichloromethane, and performing processes of organic phases combining, drying, filtering, and vacuum drying.

Performing isolation and purification by column chromatography to obtain a white powder

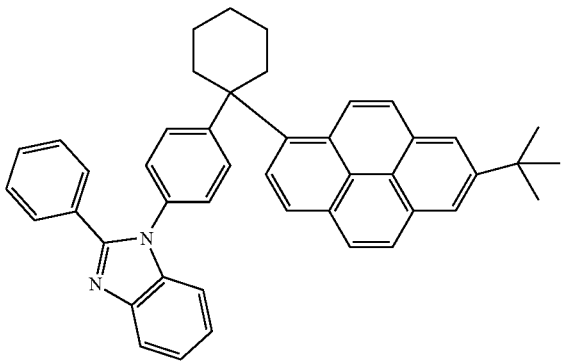 [SMILES: CC(C)(C)c1cc2ccc3ccc(C4(c5ccc(-n6c(-c7ccccc7)nc7ccccc76)cc5)CCCCC4)c4ccc(c1)c2c34]

60.79 g, yield 65%.

In the embodiment, the synthetic route of is:

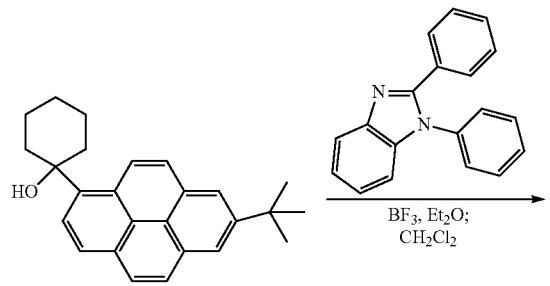

In one embodiment, the target structure of the blue fluorescent material is

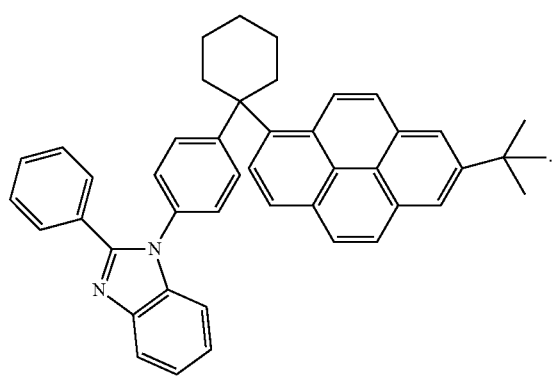

the specific steps S2 of reacting the precursor with the charge carrier transport unit include: taking

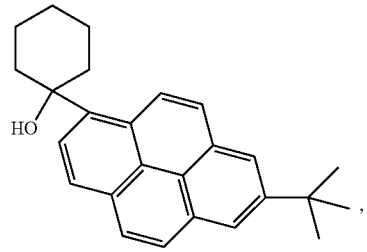

(2.2 mmol, 0.78 g)

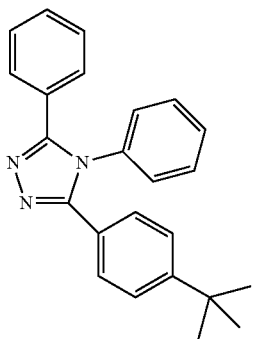

(2.0 mmol, 0.7 g)

and 100 ml of dichloromethane to a two-necked flask of 250 ml, adding BF$_3$.Et$_2$O (2.2 mmol, 0.3 ml) dropwise thereto under an Ar$_2$ atmosphere and stirring for 24 hours.

Quenching the reaction solution by adding a little amount of water, then pouring the reaction solution into a water of 100 ml, extracting for three times with dichloromethane, and performing processes of organic phases combining, drying, filtering, and vacuum drying.

Performing isolation and purification by column chromatography to obtain a white powder

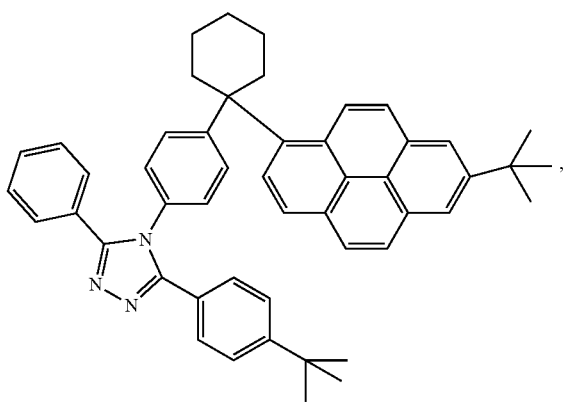 [SMILES: CC(C)(C)c1ccc(-c2nnc(-c3ccccc3)n2-c2ccc(C3(c4ccc5ccc6cc(C(C)(C)C)cc7ccc4c5c67)CCCCC3)cc2)cc1]

70.87 g, yield 65%.

In the embodiment, the synthetic route of

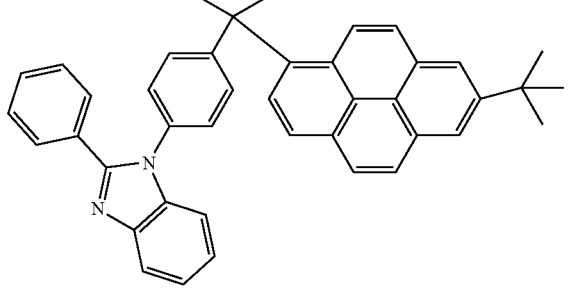

is:

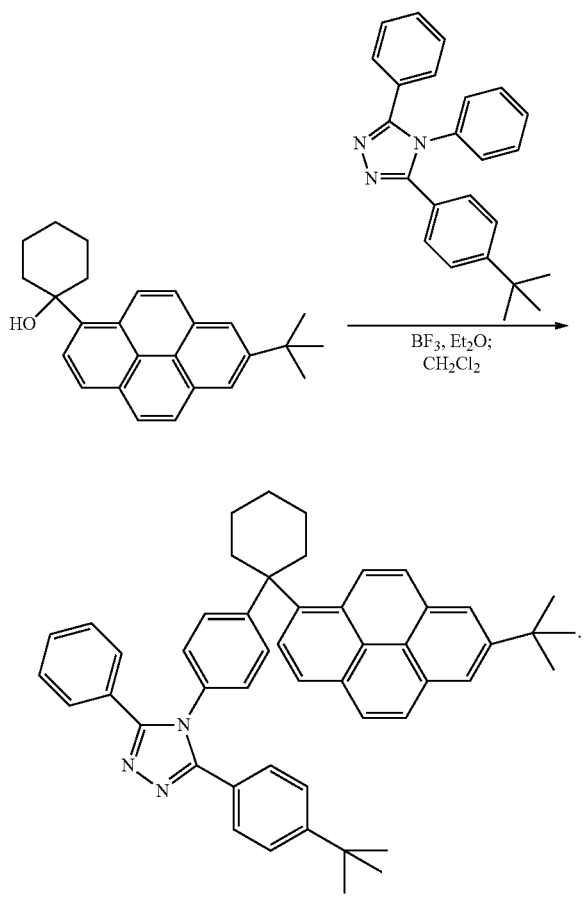

Figure 2:
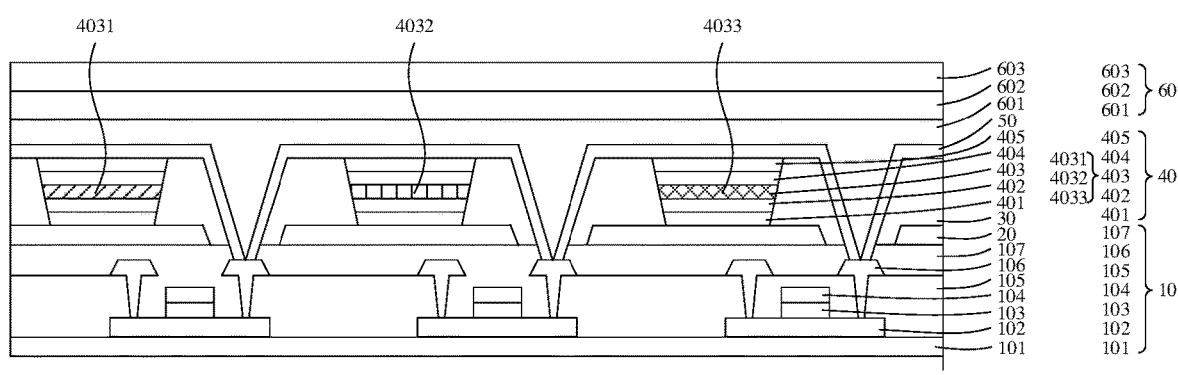
FIG. 2 is a schematic structural diagram of an OLED display panel according to an embodiment of the present disclosure.

The present application further provides an OLED display panel. In one embodiment, as shown in FIG. 2, the display panel 1 includes:

A substrate 10, in an embodiment of the present application, the substrate 10 is a TFT substrate, including a base substrate 101, a semiconductor active layer 102, a gate insulating layer 103, a gate layer 104, an interlayer insulating layer 105, a source/drain layer 106, and a passivation layer 107 which are stacked from bottom to top;

A pixel electrode layer 20 formed on the substrate 10, and is one selected from a group consisting of indium tin oxide (ITO), indium gallium zinc oxide (IGZO), zinc oxide (ZnO), tin oxide (SnO), indium zinc oxide (IZO), gallium zinc oxide (GaZnO), and zinc tin oxide (ZTO);

A pixel defining layer 30 formed on the first electrode layer 20 for defining a light emitting region;

A light-emitting function layer 40 formed in a light-emitting region of the pixel defining layer 30, including a hole injection layer 401, a hole transport layer 402, a light-emitting material layer 403, an electron transport layer 404, and an electron injection layer 405 which are stacked from bottom to top, wherein the light-emitting material layer 403 further includes a red light material layer 4031, a green light material layer 4032, and a blue light material layer 4033. The blue light material layer 4033 contains a blue fluorescent material which is a tetrahedral structure formed by simultaneously connecting a tert-butyl pyrene and a charge carrier transport unit to a same carbon of cyclohexane;

A common electrode layer 50 formed on the light-emitting function layer 40, wherein the material thereof is one or more of aluminum (Al), calcium (Ca), magnesium (Mg), and silver (Ag); and An encapsulation layer 60 formed on the second electrode layer 50, including a first inorganic layer 601, an organic layer 602, and a second inorganic layer 603.

An embodiment of the present application provides an OLED display panel, a blue light material layer of the OLED display panel includes a blue fluorescent material. The blue fluorescent material is a tetrahedral structure formed by simultaneously connecting a tert-butyl pyrene and a charge carrier transport unit to a same carbon of cyclohexane; wherein the tert-butyl pyrene increases an external quantum efficiency of the OLED display, and the tetrahedral structure increases distance between activated particles and reduces a risk of concentration quenching and greatly increases membrane fluorescence quantum efficiency. In addition, the transport unit with high charge carrier mobility improves a balance of the charge carrier transport, increases a probability of recombination, further improves the external quantum efficiency of an OLED display device, and alleviates a problem of low luminous efficiency of the current OLED display panel.

The above embodiments are references to the OLED display panel provided by the present application, but are not limited to the OLED display panel described in the above embodiments. The preparation of the OLED display panel can be carried out by methods known in the art.

In one embodiment, a structural formula of the blue fluorescent material in the blue material layer 4033 is

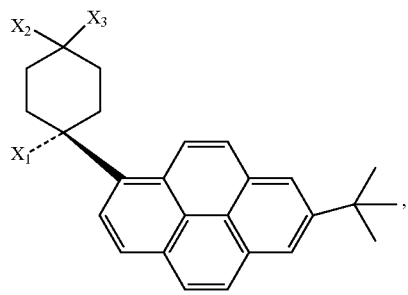

wherein the $X_1$, the $X_2$ and the $X_3$ may be the same ligand or different ligands.

In one embodiment, the $X_1$, the $X_2$, and the $X_3$ are the same ligand, and they are selected from:

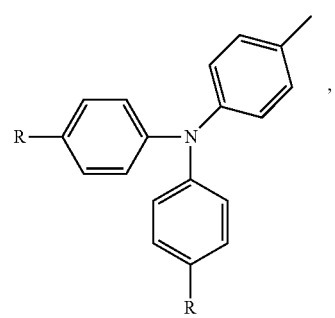

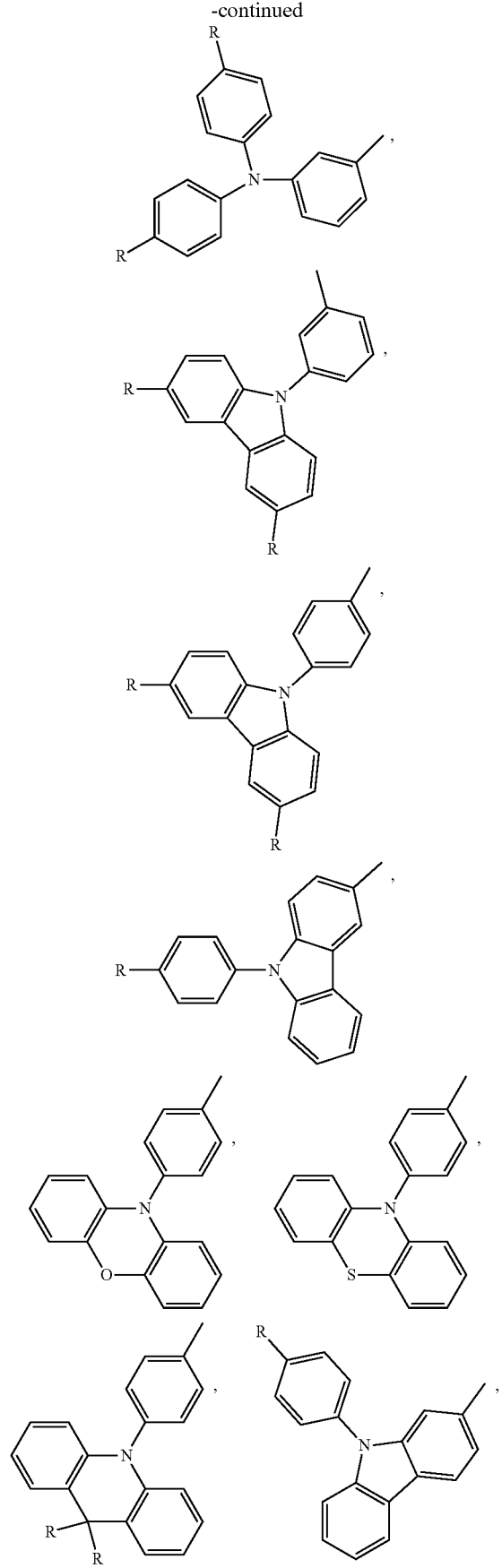
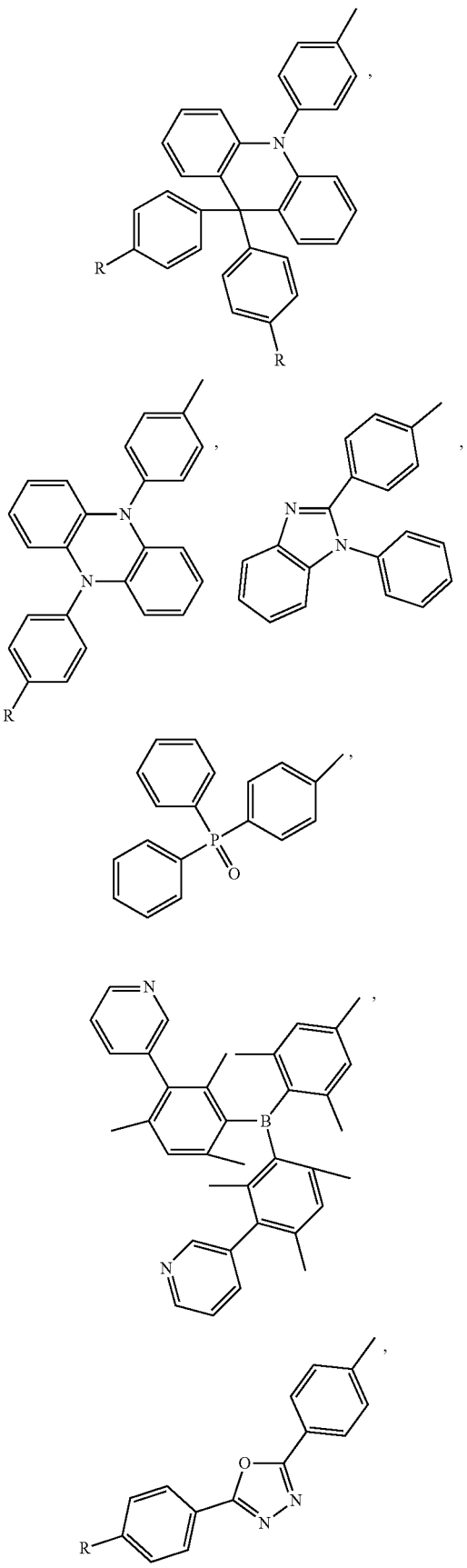

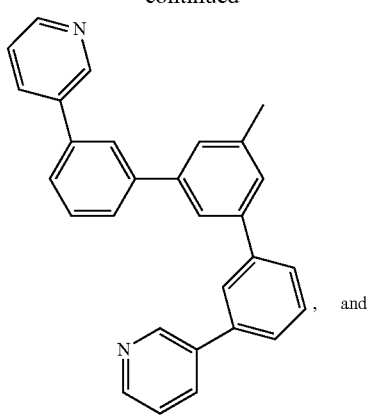
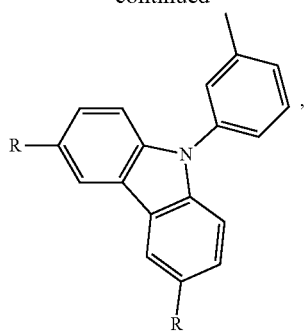
In another embodiment, the $X_1$ and the $X_2$ are the same ligand, and the
$X_1$ and the $X_3$ are different ligands, they are selected from: hydrogen,
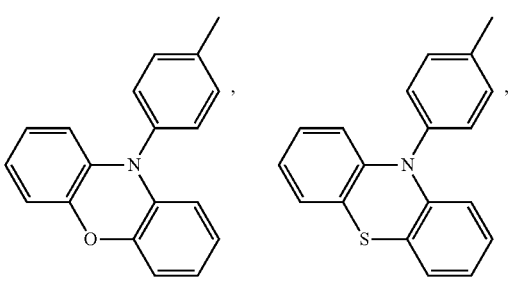
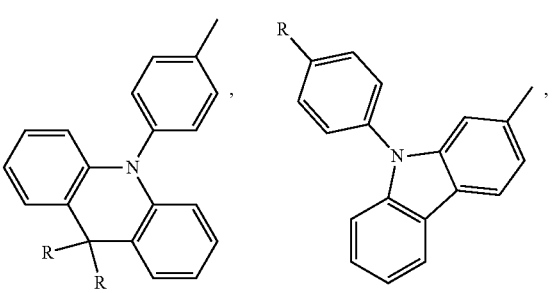

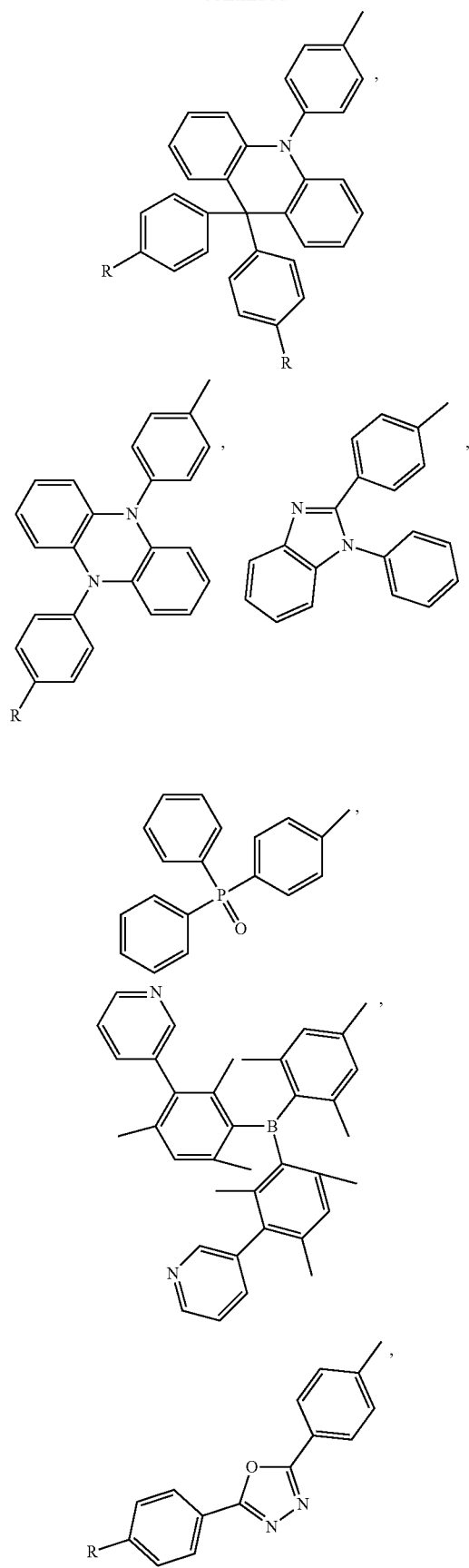
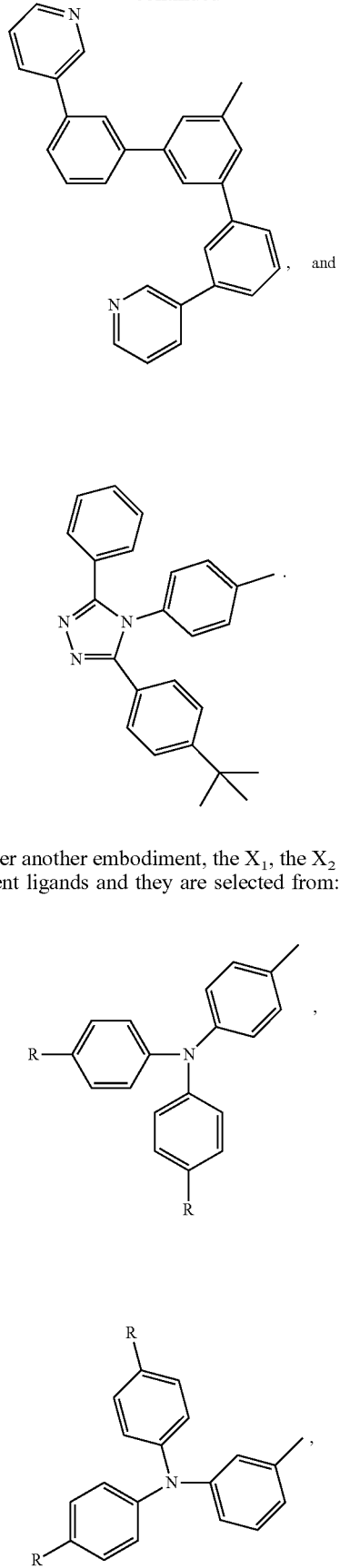
In further another embodiment, the $X_1$, the $X_2$ and the $X_3$ are different ligands and they are selected from: hydrogen,

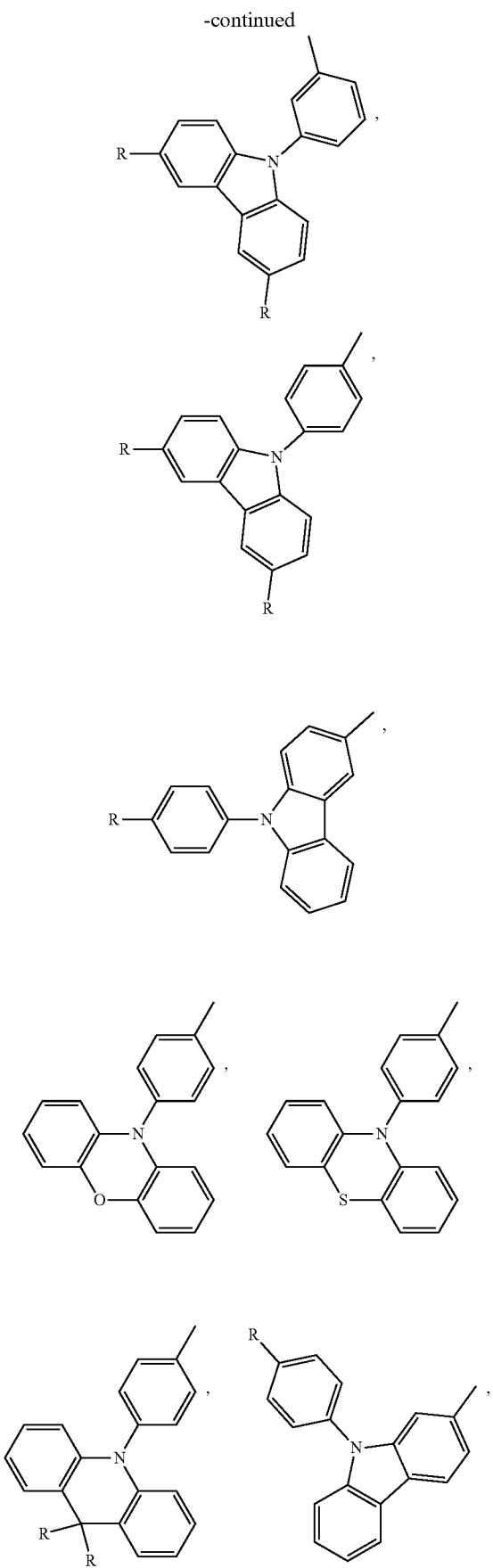
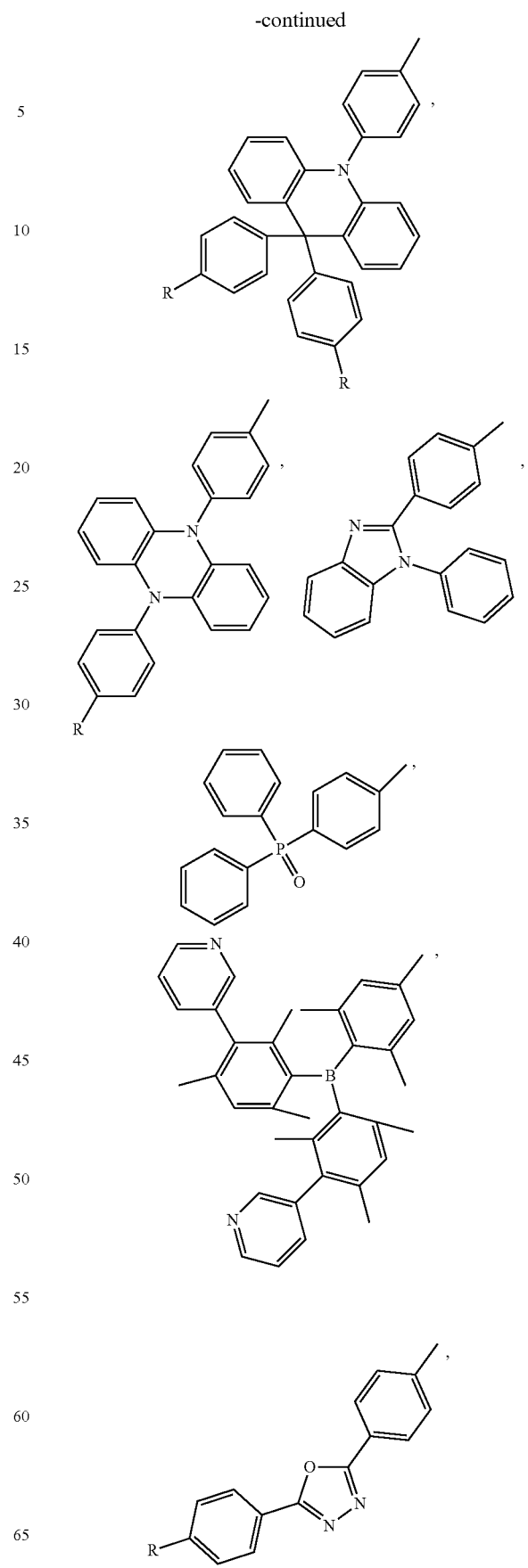

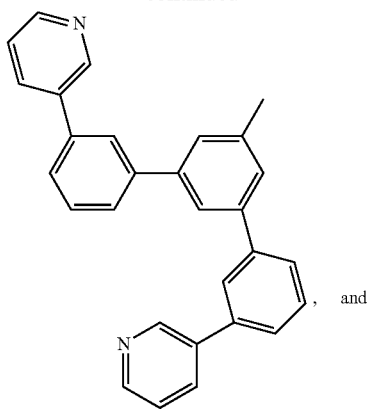
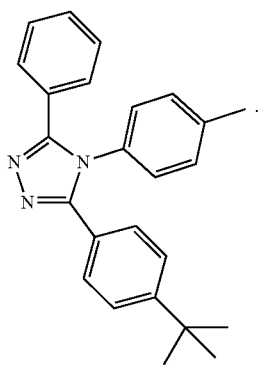
In the above embodiments, a R group of any one of
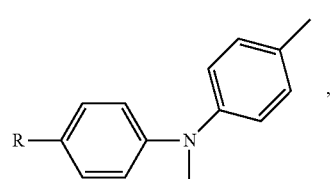
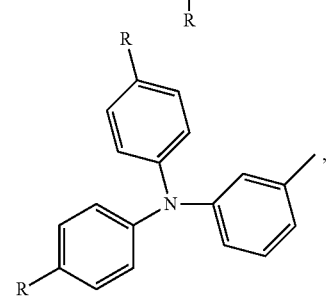
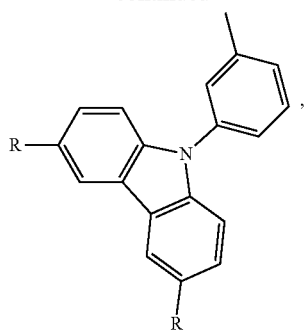
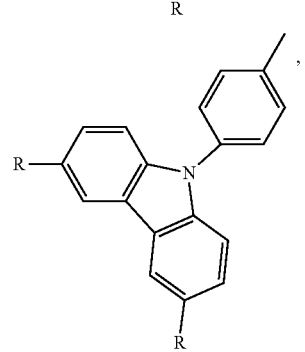
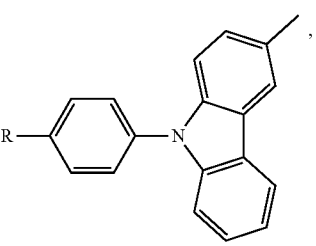
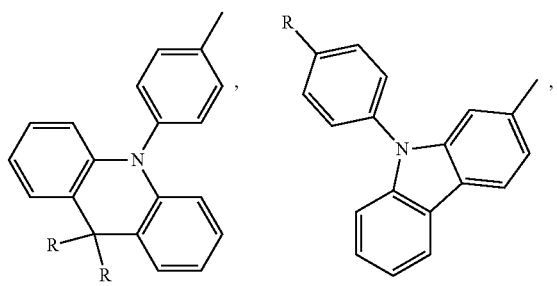
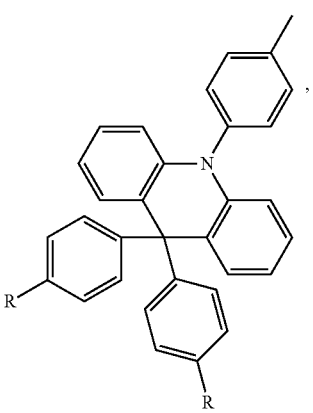

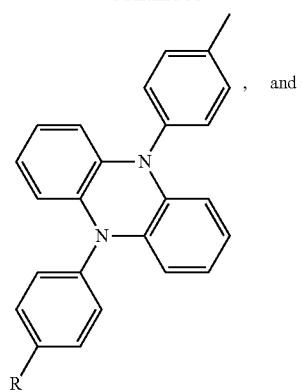
, and
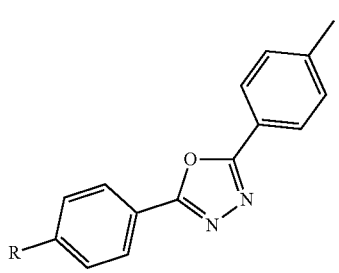
is a C1-C22 alkyl group, or a C1-C22 alkoxy group, or a C1-C22 heteroalkyl group, respectively.
A specific structure of the
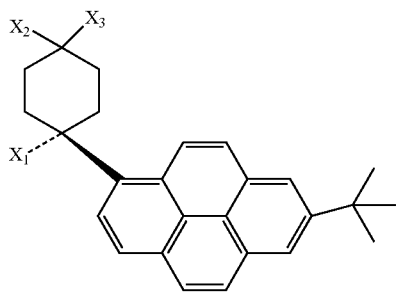
includes:
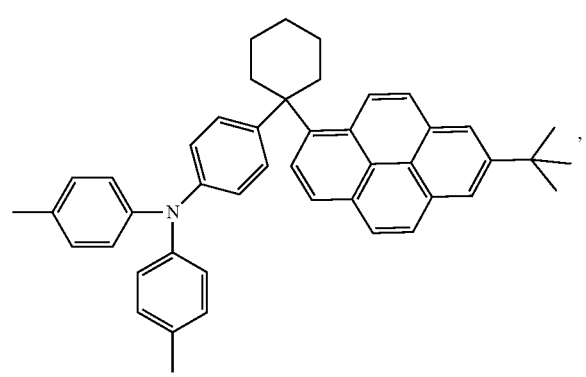
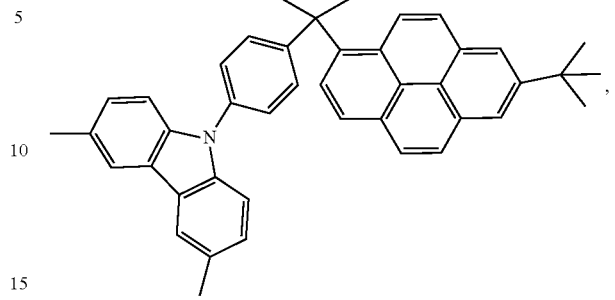
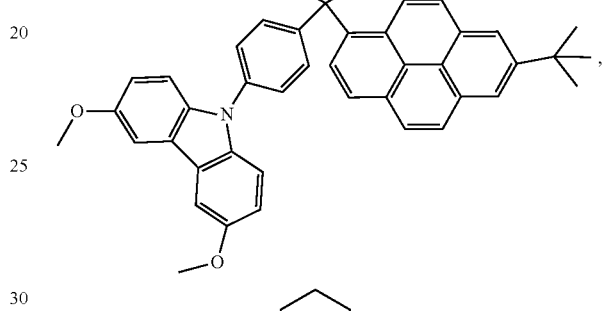
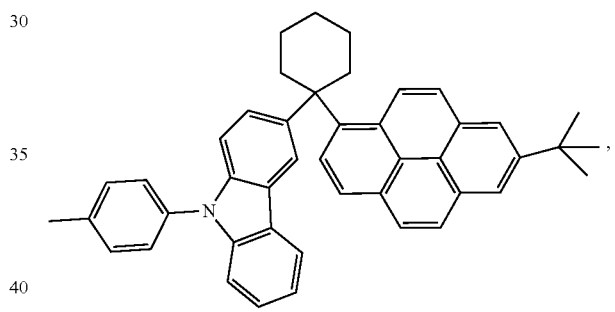
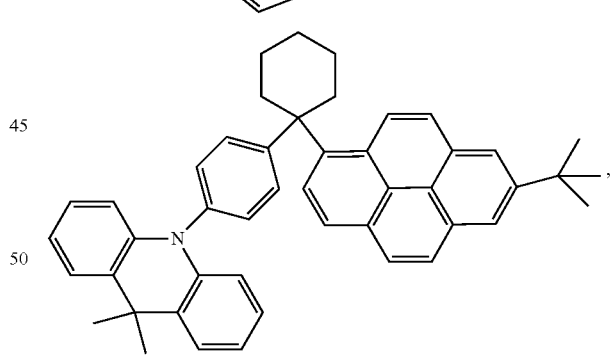
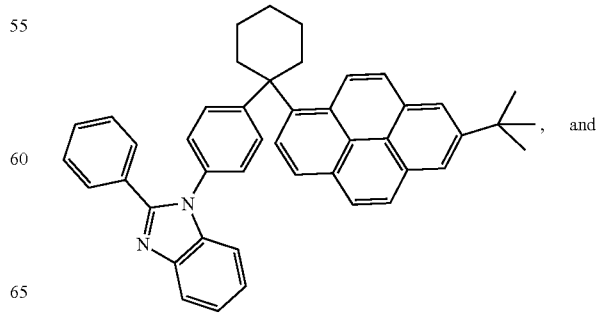
, and

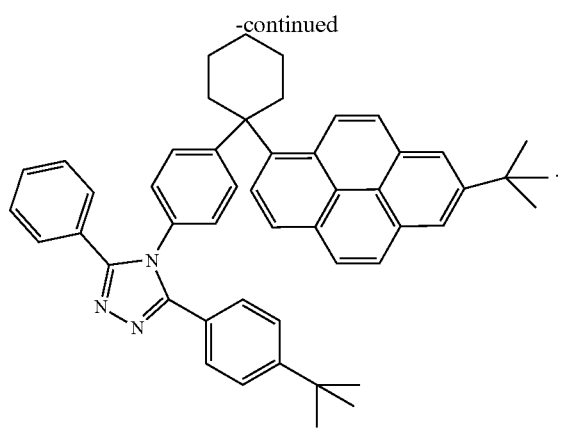

Different structures of the blue fluorescent materials have different improvement effects on the luminous efficiency of OLED display device.

In one embodiment, a material of pixel electrode layer 20 is indium tin oxide (ITO); a material of the hole injection layer 401 is poly (3,4-ethylenedioxythiophene) (PEDOT) and poly (styrenesulfonic acid) (PSS), and has a thickness of 40 nm; a material of the hole transport layer 402 is 4,4'-cyclohexyl bis [N,N-bis (4-methylphenyl) aniline (TAPC), and a thickness is 10 nm; materials of the blue light material layer 4033 are

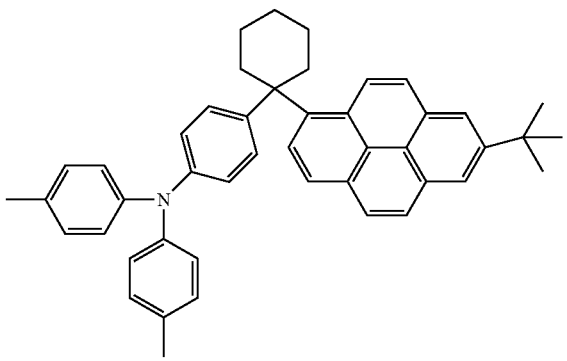 [SMILES: Cc1ccc(N(c2ccc(C)cc2)c2ccc(C3(c4ccc5ccc6cc(C(C)(C)C)cc7ccc4c5c67)CCCCC3)cc2)cc1]

and bis[2-((oxo)diphenylphosphino)phenyl]ether (DPEPO), a mass ratio of

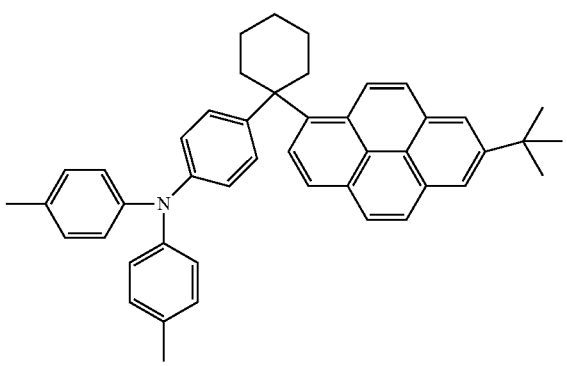 [SMILES: Cc1ccc(N(c2ccc(C)cc2)c2ccc(C3(c4ccc5ccc6cc(C(C)(C)C)cc7ccc4c5c67)CCCCC3)cc2)cc1]

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 8230 cd/m$^2$, a highest current efficiency can reach 8.12 cd/A, and the Y color coordinate is 0.19.

In one embodiment, a material of pixel electrode layer 20 is indium tin oxide (ITO); materials of the hole injection layer 401 are poly(3,4-ethylenedioxythiophene) (PEDOT) and poly(styrenesulfonic acid) (PSS), and has a thickness of 40 nm; a material of the hole transport layer 402 is 4,4'-cyclohexyl bis[N,N-bis(4-methylphenyl)aniline (TAPC), and a thickness is 10 nm; materials of the blue light material layer 4033 are

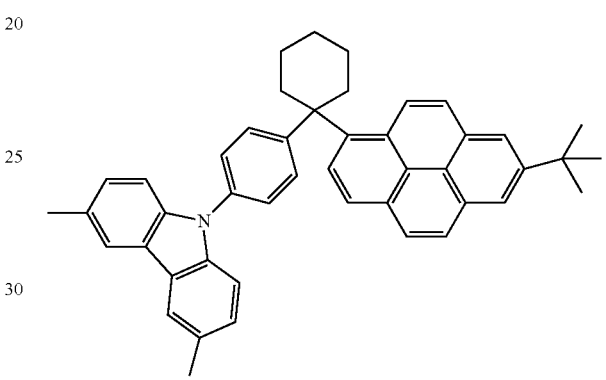

and bis [2-((oxo)diphenylphosphino)phenyl]ether (DPEPO), a mass ratio of

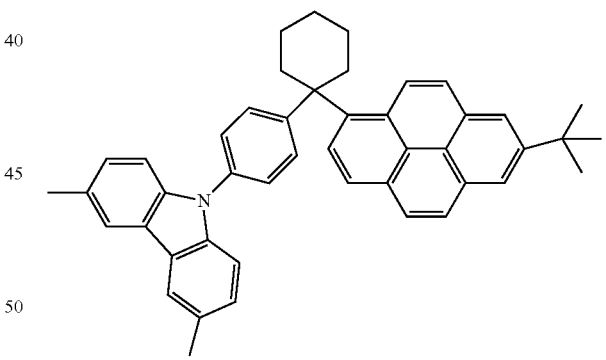

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 8740 cd/m$^2$, a highest current efficiency can reach 8.14 cd/A, and the Y color coordinate is 0.23.

In one embodiment, a material of pixel electrode layer 20 is indium tin oxide (ITO); materials of the hole injection layer 401 are poly(3,4-ethylenedioxythiophene) (PEDOT) and poly(styrenesulfonic acid) (PSS), and has a thickness of 40 nm; a material of the hole transport layer 402 is 4,4'-cyclohexyl bis[N,N-bis(4-methylphenyl)aniline (TAPC), and a thickness is 10 nm; materials of the blue light material layer 4033 are

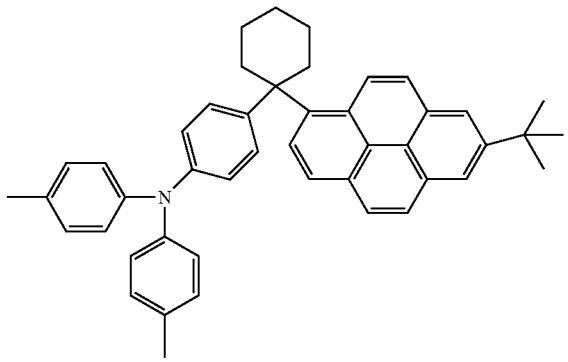 [SMILES: Cc1ccc(N(c2ccc(C)cc2)c2ccc(C3(c4ccc5ccc6cc(C(C)(C)C)cc7ccc4c5c67)CCCCC3)cc2)cc1]

and bis[2-((oxo)diphenylphosphino)phenyl]ether (DPEPO), a mass ratio of

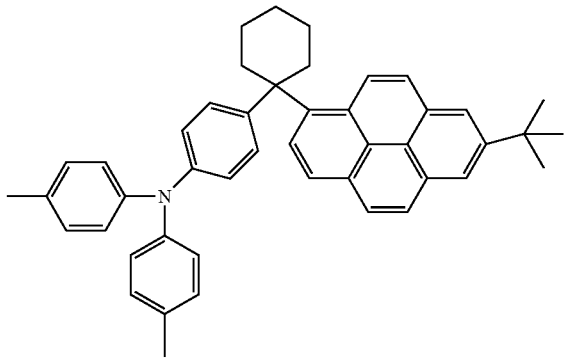 [SMILES: Cc1ccc(N(c2ccc(C)cc2)c2ccc(C3(c4ccc5ccc6cc(C(C)(C)C)cc7ccc4c5c67)CCCCC3)cc2)cc1]

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 8230 cd/m², a highest current efficiency can reach 8.12 cd/A, and Y color coordinate is 0.19.

In one embodiment, a material of pixel electrode layer 20 is indium tin oxide (ITO); materials of the hole injection layer 401 are poly(3,4-ethylenedioxythiophene) (PEDOT) and poly(styrenesulfonic acid) (PSS), and has a thickness of 40 nm; a material of the hole transport layer 402 is 4,4'-cyclohexyl bis[N,N-bis(4-methylphenyl)aniline (TAPC), and a thickness is 10 nm; materials of the blue light material layer 4033 are

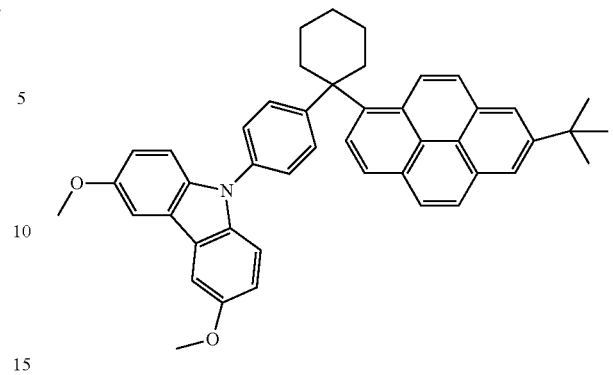

and bis[2-((oxo)diphenylphosphino)phenyl]ether (DPEPO), a mass ratio of

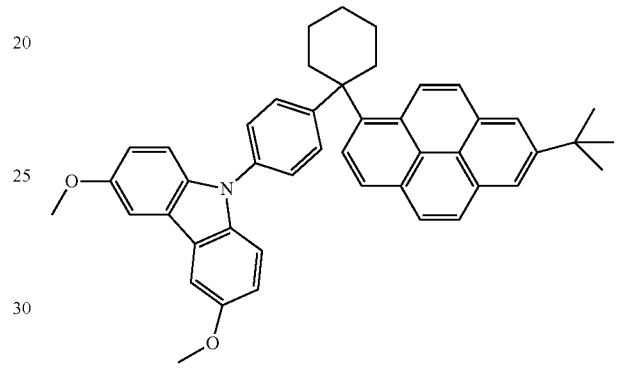

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 6770 cd/m², a highest current efficiency can reach 5.9 cd/A, and Y color coordinate is 0.16.

In one embodiment, a material of pixel electrode layer 20 is indium tin oxide (ITO); materials of the hole injection layer 401 are poly(3,4-ethylenedioxythiophene) (PEDOT) and poly(styrenesulfonic acid) (PSS), and has a thickness of 40 nm; a material of the hole transport layer 402 is 4,4'-cyclohexyl bis[N,N-bis(4-methylphenyl)aniline (TAPC), and a thickness is 10 nm; materials of the blue light material layer 4033 are

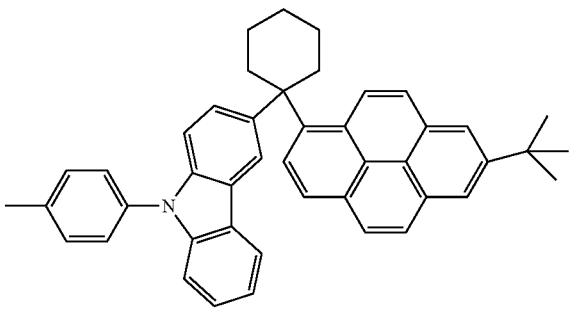 [SMILES: Cc1ccc(-n2c3ccccc3c3cc(C4(c5ccc6ccc7cc(C(C)(C)C)cc8ccc5c6c78)CCCCC4)ccc32)cc1]

and bis[2-((oxo)diphenylphosphino)phenyl]ether (DPEPO), a mass ratio of

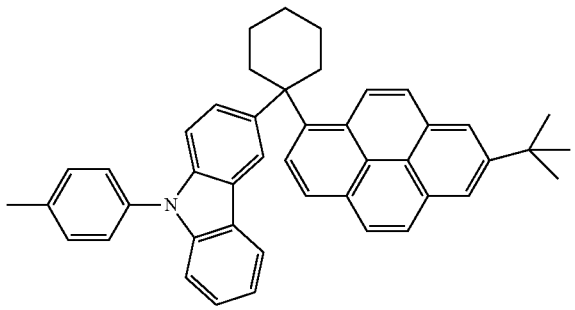 [SMILES: Cc1ccc(-n2c3ccccc3c3cc(C4(c5ccc6ccc7cc(C(C)(C)C)cc8ccc5c6c78)CCCCC4)ccc32)cc1]

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 5740 $cd/m^2$, a highest current efficiency can reach 5.35 cd/A, and Y color coordinate is 0.14.

In one embodiment, a material of pixel electrode layer 20 is indium tin oxide (ITO); materials of the hole injection layer 401 are poly(3,4-ethylenedioxythiophene) (PEDOT) and poly(styrenesulfonic acid) (PSS), and has a thickness of 40 nm; a material of the hole transport layer 402 is 4,4'-cyclohexyl bis[N,N-bis(4-methylphenyl)aniline (TAPC), and a thickness is 10 nm; materials of the blue light material layer 4033 are

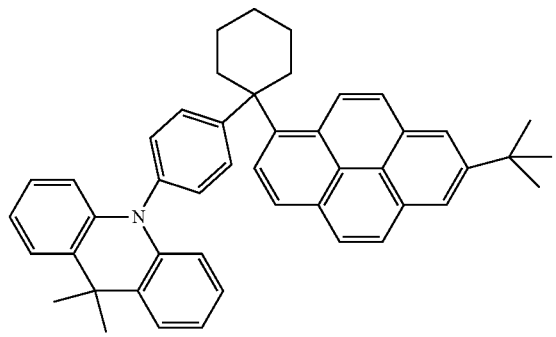 [SMILES: CC(C)(C)c1cc2ccc3ccc(C4(c5ccc(N6c7ccccc7C(C)(C)c7ccccc76)cc5)CCCCC4)c4ccc(c1)c2c34]

and bis[2-((oxo)diphenylphosphino)phenyl]ether (DPEPO), a mass ratio of

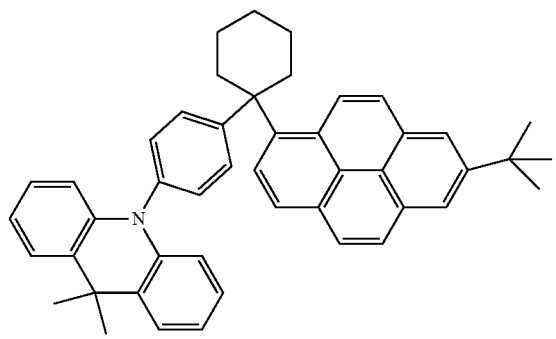 [SMILES: CC(C)(C)c1cc2ccc3ccc(C4(c5ccc(N6c7ccccc7C(C)(C)c7ccccc76)cc5)CCCCC4)c4ccc(c1)c2c34]

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 8750 $cd/m^2$, a highest current efficiency can reach 7.84 cd/A, and Y color coordinate is 0.18.

In one embodiment, a material of pixel electrode layer 20 is indium tin oxide (ITO); materials of the hole injection layer 401 are poly(3,4-ethylenedioxythiophene) (PEDOT) and poly(styrenesulfonic acid) (PSS), and has a thickness of 40 nm; a material of the hole transport layer 402 is 4,4'-cyclohexyl bis[N,N-bis(4-methylphenyl)aniline (TAPC), and a thickness is 10 nm; materials of the blue light material layer 4033 are

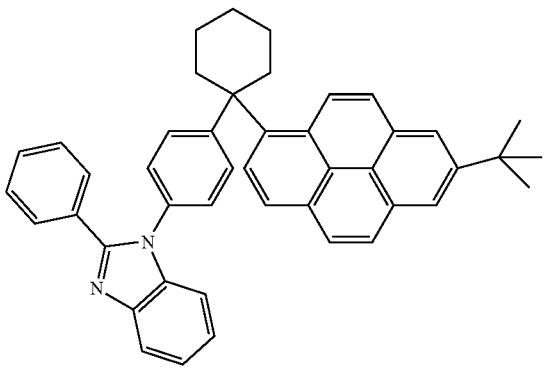 [SMILES: CC(C)(C)c1cc2ccc3ccc(C4(c5ccc(-n6c(-c7ccccc7)nc7ccccc76)cc5)CCCCC4)c4ccc(c1)c2c34]

and bis[2-((oxo)diphenylphosphino)phenyl]ether (DPEPO), a mass ratio of

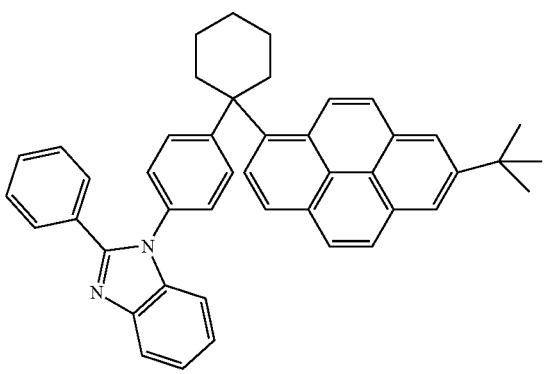 [SMILES: CC(C)(C)c1cc2ccc3ccc(C4(c5ccc(-n6c(-c7ccccc7)nc7ccccc76)cc5)CCCCC4)c4ccc(c1)c2c34]

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 7430 $cd/m^2$, a highest current efficiency can reach 6.5 cd/A, and Y color coordinate is 0.17.

In one embodiment, a material of pixel electrode layer 20 is indium tin oxide (ITO); materials of the hole injection layer 401 are poly(3,4-ethylenedioxythiophene) (PEDOT) and poly(styrenesulfonic acid) (PSS), and has a thickness of 40 nm; a material of the hole transport layer 402 is 4,4'-cyclohexyl bis[N,N-bis(4-methylphenyl)aniline (TAPC), and a thickness is 10 nm; materials of the blue light material layer 4033 are

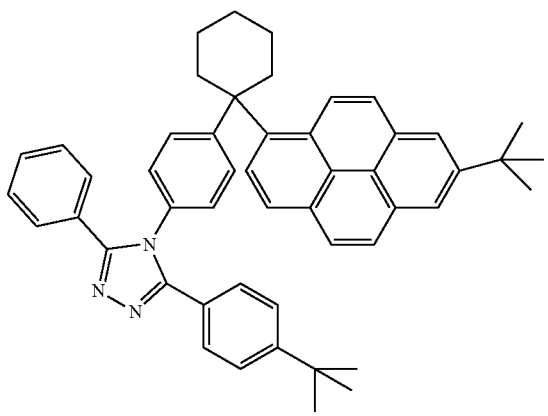 [SMILES: CC(C)(C)c1ccc(-c2nnc(-c3ccccc3)n2-c2ccc(C3(c4ccc5ccc6cc(C(C)(C)C)cc7ccc4c5c67)CCCCC3)cc2)cc1]

and bis[2-((oxo)diphenylphosphino)phenyl]ether (DPEPO), a mass ratio of

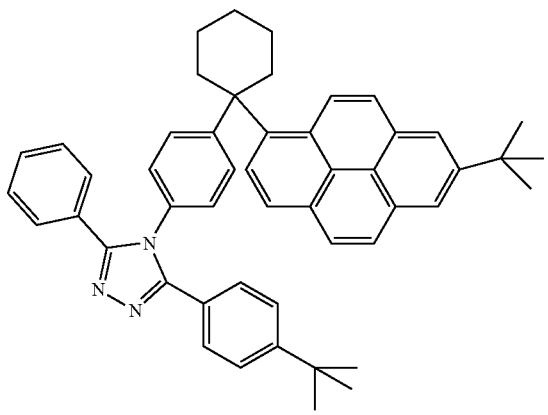 [SMILES: CC(C)(C)c1ccc(-c2nnc(-c3ccccc3)n2-c2ccc(C3(c4ccc5ccc6cc(C(C)(C)C)cc7ccc4c5c67)CCCCC3)cc2)cc1]

to the entire blue light material layer 4033 is 4% and a thickness of the blue light material layer 4033 is 20 nm; a material of the electron transport layer 404 is 1,3,5-tris[(3-pyridyl)-3-phenyl]benzene (TmPyPB), and has a thickness of 30 nm; a material of the electron injection layer 405 is lithium fluoride (LiF) and has a thickness of 1 nm; and a material of the common electrode layer 50 is metal aluminum (Al) and has a thickness of 100 nm.

In the embodiment, a maximum brightness of the OLED display device can reach 7640 cd/m², a highest current efficiency can reach 6.91 cd/A, and Y color coordinate is 0.2.

According to the above embodiments, it can be known that the present application provides a blue fluorescent material and an OLED display panel, the blue fluorescent material is a tetrahedral structure formed by simultaneously connecting a tert-butyl pyrene and a charge carrier transport unit to a same carbon of cyclohexane, wherein the tert-butyl pyrene increases an external quantum efficiency of the OLED display, and the tetrahedral structure increases distance between activated particles and reduces a risk of concentration quenching and greatly increases membrane fluorescence quantum efficiency. In addition, the transport unit with high charge carrier mobility improves a balance of the charge carrier transport, increases a probability of recombination, further improves an external quantum efficiency of an OLED display device, and alleviates a problem of low luminous efficiency of the current OLED display panel.

The description of the above exemplary embodiments is only for the purpose of understanding the invention. It is to be understood that the present invention is not limited to the disclosed exemplary embodiments. It is obvious to those skilled in the art that the above exemplary embodiments may be modified without departing from the scope and spirit of the present invention.

What is claimed is:

1. A blue fluorescent material represented by a chemical formula of:

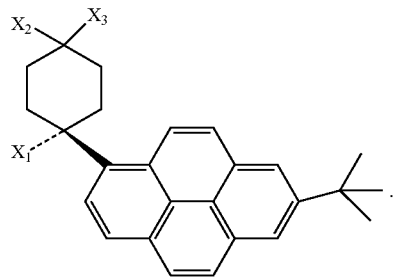

wherein $X_1$, $X_2$, and $X_3$ each is selected from one of

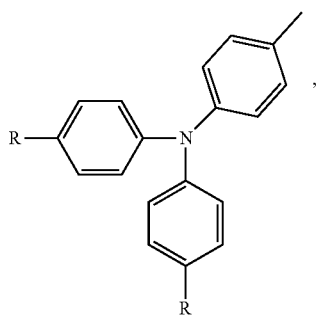

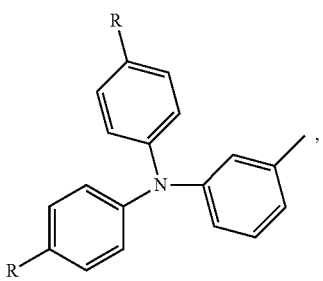

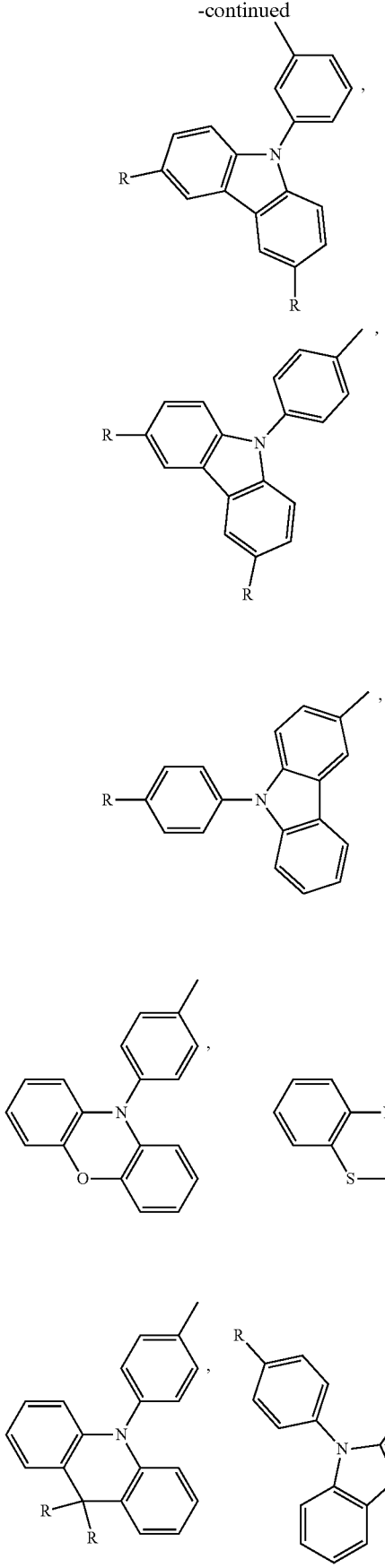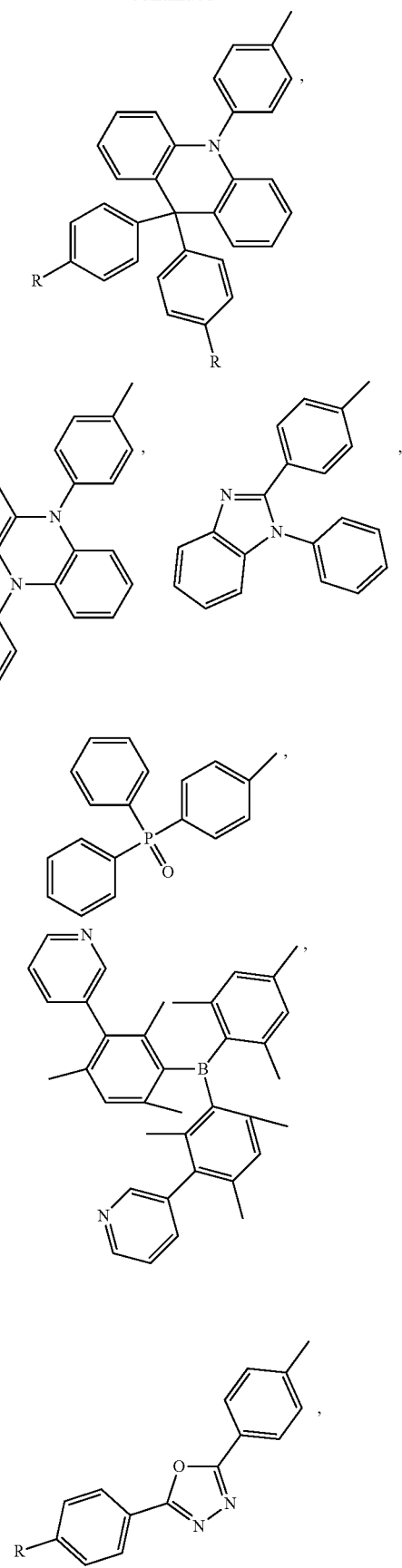

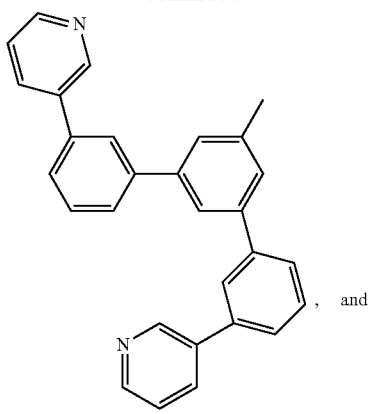
, and
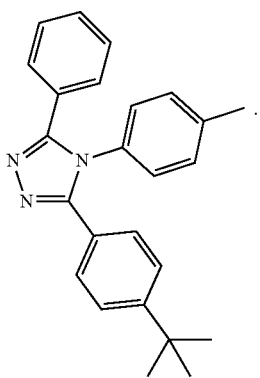
and wherein R of any of the
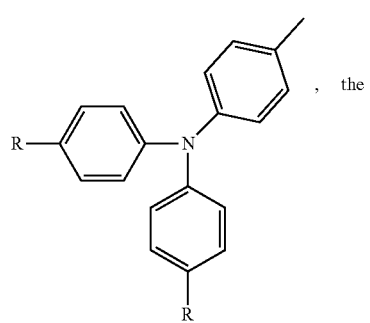
, the
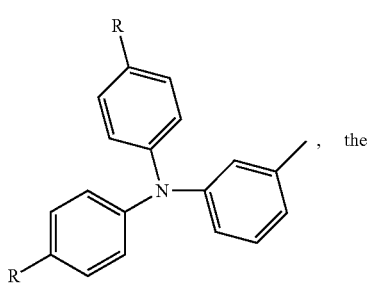
, the
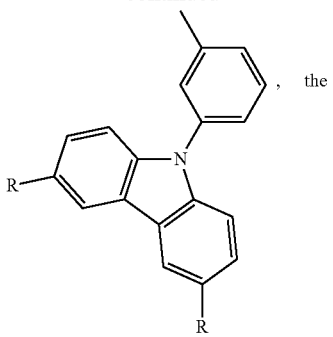
, the
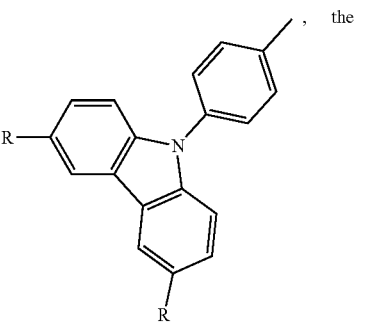
, the
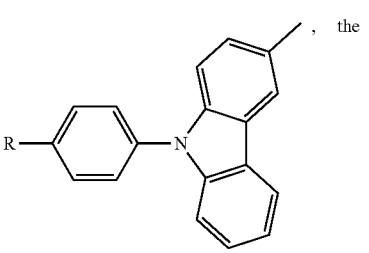
, the
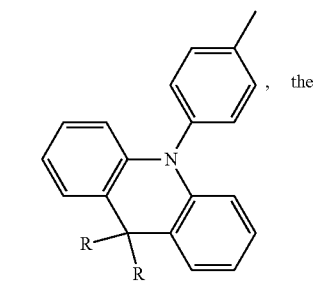
, the
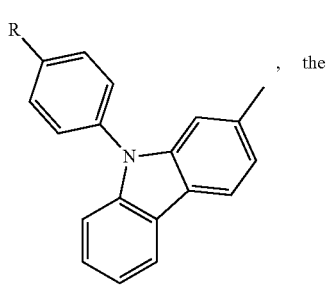
, the -continued
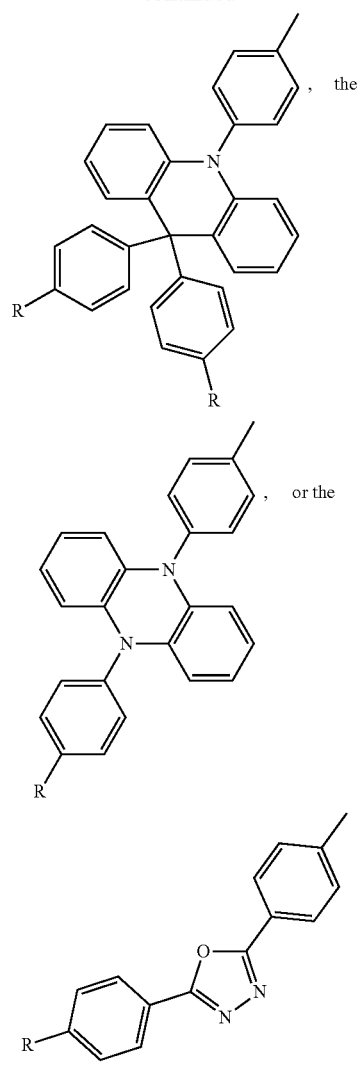
is selected from an alkyl group having carbon atoms ranging from 1 to 22, an alkoxy group having carbon atoms ranging from 1 to 22, or a heteroalkyl group having carbon atoms ranging from 1 to 22.
2. A blue fluorescent material represented by a chemical formula of:
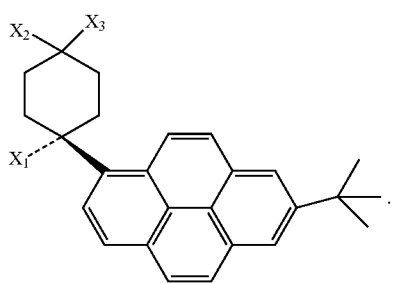
wherein $X_1$ is selected from any of
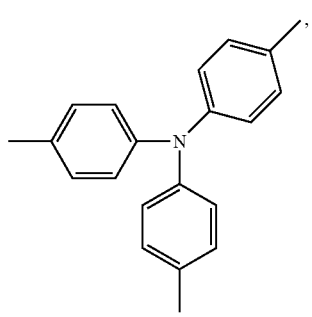
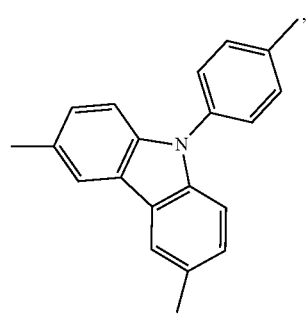
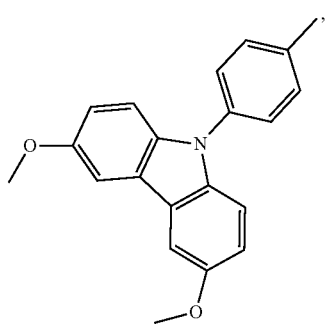
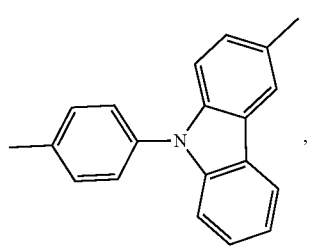
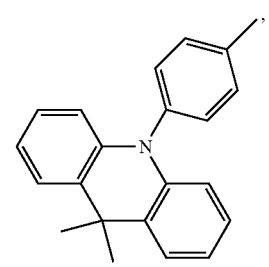

71
-continued
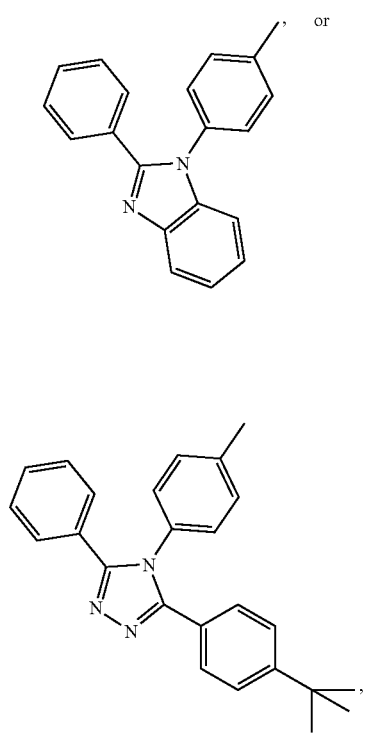
and $X_2$ and $X_3$ each is a hydrogen atom.
3. A blue fluorescent material represented by a chemical formula of:
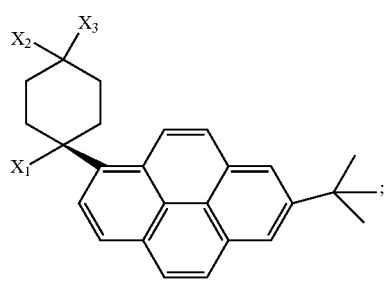
wherein $X_1$ is selected from any of
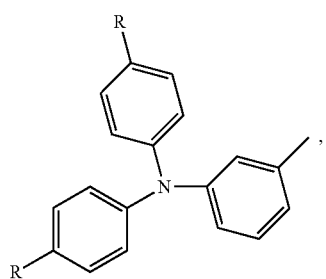
72
-continued
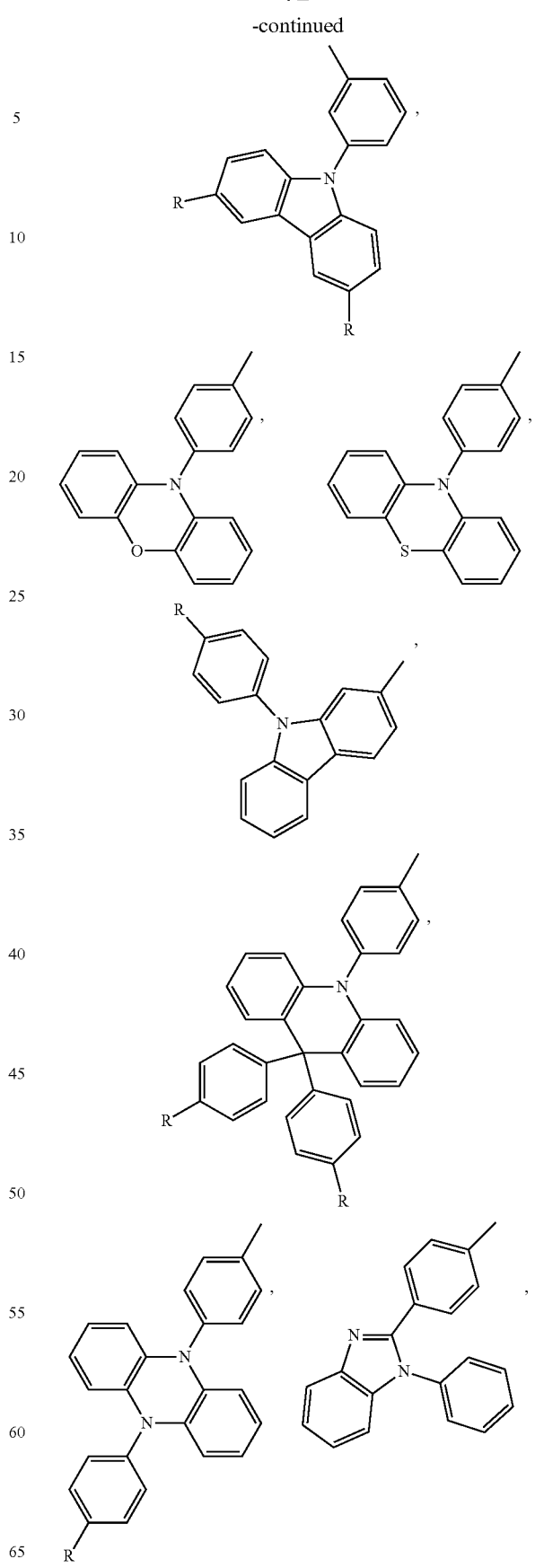

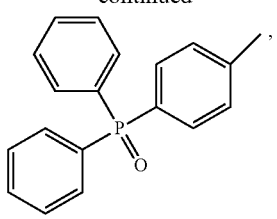
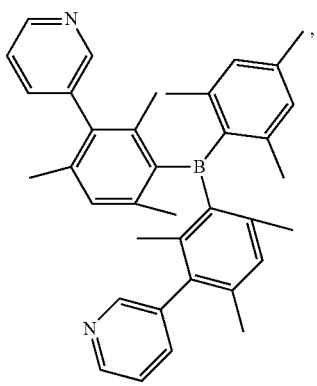
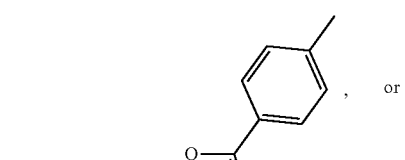, or
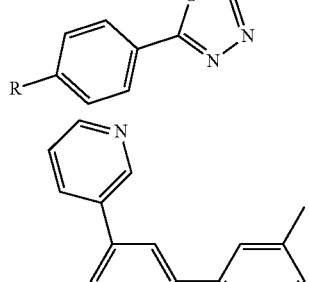
and $X_2$ and $X_3$ each is a hydrogen atom; and wherein R of any of the
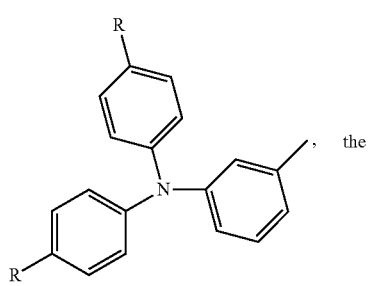, the
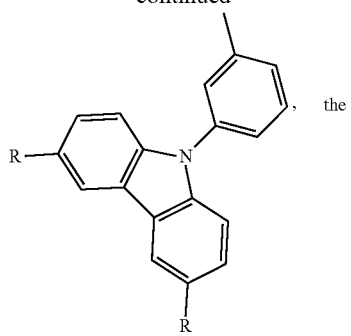, the
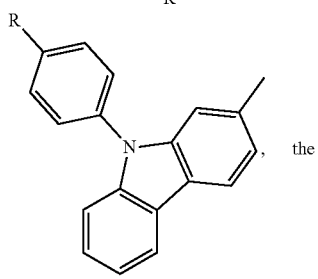, the
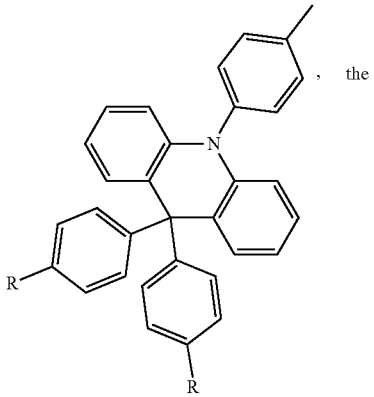, the
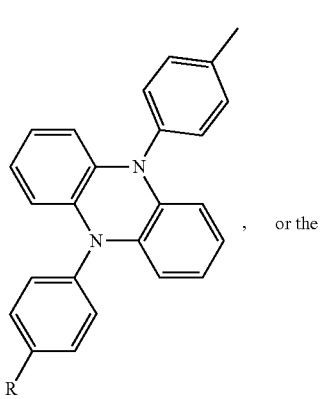, or the
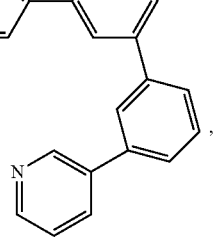

is selected from an alkyl group having carbon atoms ranging from 1 to 22, an alkoxy group having carbon atoms ranging from 1 to 22, or a heteroalkyl group having carbon atoms ranging from 1 to 22.

* * * * *